(12) United States Patent
Thompson et al.

(10) Patent No.: US 9,707,184 B2
(45) Date of Patent: Jul. 18, 2017

(54) IMMEDIATE RELEASE ABUSE DETERRENT LIQUID FILL DOSAGE FORM

(71) Applicant: Pharmaceutical Manufacturing Research Services, Inc., Horsham, PA (US)

(72) Inventors: Edwin R. Thompson, Horsham, PA (US); Eric R. Thompson, Chalfont, PA (US); Nicholas R. Myslinski, Bensalem, PA (US); Steven F. Kemeny, Philadelphia, PA (US); Matthew N. Hart, Palmyra, NJ (US)

(73) Assignee: Pharmaceutical Manufacturing Research Services, Inc., Horsham, PA (US)

( * ) Notice: Subject to any disclaimer, the term of this patent is extended or adjusted under 35 U.S.C. 154(b) by 0 days.

(21) Appl. No.: 14/792,699

(22) Filed: Jul. 7, 2015

(65) Prior Publication Data
US 2016/0015650 A1 Jan. 21, 2016

Related U.S. Application Data

(60) Provisional application No. 62/025,878, filed on Jul. 17, 2014.

(51) Int. Cl.
*A61K 31/485* (2006.01)
*A61K 9/48* (2006.01)

(52) U.S. Cl.
CPC .......... *A61K 9/4866* (2013.01); *A61K 9/4833* (2013.01); *A61K 9/4858* (2013.01); *A61K 31/485* (2013.01)

(58) Field of Classification Search
CPC .................................................. A61K 9/4866
See application file for complete search history.

(56) References Cited

U.S. PATENT DOCUMENTS

| | | |
|---|---|---|
| 3,439,069 A | 4/1969 | Cherkas et al. |
| 4,450,877 A | 5/1984 | Walker et al. |
| 5,141,961 A | 8/1992 | Coapman |
| 5,202,128 A | 4/1993 | Morella et al. |
| 5,266,331 A | 11/1993 | Oshlack et al. |
| 5,431,916 A | 7/1995 | White |
| 5,458,879 A | 10/1995 | Singh et al. |
| 5,614,218 A | 3/1997 | Olsson et al. |

(Continued)

FOREIGN PATENT DOCUMENTS

| | | |
|---|---|---|
| CA | 264736 A | 10/1926 |
| CA | 265145 A | 10/1926 |

(Continued)

OTHER PUBLICATIONS

Third Party Observation dated Sep. 8, 2015 for International Application No. PCT/US2014/050737.
Gazzaniga et al., "A novel injection-molded capsular device for oral pulsatile delivery based on swellable/erodible polymers", AAPS PharmSciTech, 2011, vol. 12, No. 1, pp. 295-303.
Soininen et al., "Effect of polyethylene glycol 20000 on bioavailability of micronized and crystalline paracetamol", Acta Pharmaceutica Fennica, 1981, vol. 90, vol. 4, pp. 381-386.

(Continued)

*Primary Examiner* — Adam C Milligan
*Assistant Examiner* — Sarah Alawadi
(74) *Attorney, Agent, or Firm* — McCarter & English, LLP; Elizabeth A. Hanley; Yu Lu

(57) ABSTRACT

The present disclosure relates to an oral, immediate release, abuse deterrent liquid filled capsule containing polyethylene glycol and at least one active pharmaceutical ingredient susceptible to abuse. The dosage form is abuse deterrent to parenteral administration. The present disclosure also relates to processes of preparing the dosage form.

16 Claims, 4 Drawing Sheets

(56) References Cited

U.S. PATENT DOCUMENTS

| | | |
|---|---|---|
| 5,616,621 A | 4/1997 | Popli et al. |
| 5,827,852 A | 10/1998 | Russell et al. |
| 5,840,337 A | 11/1998 | Cody et al. |
| 5,840,731 A | 11/1998 | Mayer et al. |
| 5,866,164 A | 2/1999 | Kuczynski et al. |
| 5,914,129 A | 6/1999 | Mauskop |
| 6,024,980 A | 2/2000 | Hoy |
| 6,068,855 A | 5/2000 | Leslie et al. |
| 6,102,254 A | 8/2000 | Ross |
| 6,159,501 A | 12/2000 | Skinhoj |
| 6,160,020 A | 12/2000 | Ohannesian et al. |
| 6,190,591 B1 | 2/2001 | van Lengerich |
| 6,207,674 B1 | 3/2001 | Smith |
| 6,245,357 B1 | 6/2001 | Edgren et al. |
| 6,251,430 B1 | 6/2001 | Zhang et al. |
| 6,277,384 B1 | 8/2001 | Kaiko et al. |
| 6,309,669 B1 | 10/2001 | Setterstrom et al. |
| 6,432,450 B1 | 8/2002 | Gergely et al. |
| 6,488,963 B1 | 12/2002 | McGinity et al. |
| 6,500,459 B1 | 12/2002 | Chhabra et al. |
| 6,572,891 B1 | 6/2003 | Ugarkovic |
| 6,627,635 B2 | 9/2003 | Palermo et al. |
| 6,706,281 B2 | 3/2004 | Oshlack et al. |
| 6,713,470 B2 | 3/2004 | Jackson |
| 6,740,333 B2 | 5/2004 | Beckett et al. |
| 6,753,009 B2 | 6/2004 | Luber et al. |
| 6,800,668 B1 | 10/2004 | Odidi et al. |
| 6,869,618 B2 | 3/2005 | Kiel et al. |
| 6,905,709 B2 | 6/2005 | Oshlack et al. |
| 6,923,988 B2 | 8/2005 | Patel et al. |
| 7,141,250 B2 | 11/2006 | Oshlack et al. |
| 7,201,920 B2 | 4/2007 | Kumar et al. |
| 7,214,385 B2 | 5/2007 | Gruber |
| 7,316,821 B2 | 1/2008 | Oshlack et al. |
| 7,384,653 B2 | 6/2008 | Wright, IV et al. |
| 7,413,750 B2 | 8/2008 | Kolter et al. |
| 7,514,100 B2 | 4/2009 | Oshlack et al. |
| 7,544,676 B2 | 6/2009 | Dolle et al. |
| 7,655,256 B2 | 2/2010 | Hughes |
| 7,666,337 B2 | 2/2010 | Yang et al. |
| 7,670,612 B2 | 3/2010 | Miller |
| 7,670,627 B2 | 3/2010 | Shefer et al. |
| 7,718,194 B2 | 5/2010 | Chenevier et al. |
| 7,744,916 B2 | 6/2010 | Pauletti et al. |
| 7,754,240 B2 | 7/2010 | Staniforth et al. |
| 7,780,987 B2 | 8/2010 | Zhou et al. |
| 7,790,215 B2 | 9/2010 | Sackler et al. |
| 7,842,307 B2 | 11/2010 | Oshlack et al. |
| 7,846,460 B2 | 12/2010 | Chenevier et al. |
| 7,846,476 B2 | 12/2010 | Oshlack et al. |
| 7,910,128 B2 | 3/2011 | Chang et al. |
| 7,943,173 B2 | 5/2011 | Breder et al. |
| 7,968,119 B2 | 6/2011 | Farrell |
| 8,029,822 B2 | 10/2011 | Faour et al. |
| 8,075,872 B2 | 12/2011 | Arkenau-Maric et al. |
| 8,114,383 B2 | 2/2012 | Bartholomaus et al. |
| 8,124,126 B2 | 2/2012 | Bosse et al. |
| 8,133,507 B2 | 3/2012 | Yum et al. |
| 8,138,169 B2 | 3/2012 | Oronsky et al. |
| 8,143,267 B2 | 3/2012 | Burch et al. |
| 8,188,108 B2 | 5/2012 | Mayo-Alvarez et al. |
| 8,202,542 B1 | 6/2012 | Mehta et al. |
| 8,216,610 B2 | 7/2012 | Roberts et al. |
| 8,263,125 B2 | 9/2012 | Vaya et al. |
| 8,313,757 B2 | 11/2012 | van Lengerich |
| 8,318,105 B2 | 11/2012 | Selinfreund et al. |
| 8,318,641 B2 | 11/2012 | Selinfreund et al. |
| 8,333,989 B2 | 12/2012 | Sukuru |
| 8,337,888 B2 | 12/2012 | Wright et al. |
| 8,362,029 B2 | 1/2013 | Evenstad et al. |
| 8,377,453 B2 | 2/2013 | Han et al. |
| 8,383,152 B2 | 2/2013 | Jans et al. |
| 8,394,813 B2 | 3/2013 | Mickle et al. |
| 8,415,401 B2 | 4/2013 | Yum et al. |
| 8,420,114 B2 | 4/2013 | Zanella et al. |
| 8,426,411 B2 | 4/2013 | Wishart et al. |
| 8,445,023 B2 | 5/2013 | Guimberteau et al. |
| 8,465,776 B2 | 6/2013 | Hoarau |
| 8,481,560 B2 | 7/2013 | Stinchcomb et al. |
| 8,486,448 B2 | 7/2013 | Rahmouni et al. |
| 8,486,449 B2 | 7/2013 | Rahmouni et al. |
| 8,497,303 B2 | 7/2013 | Wurn et al. |
| 8,501,160 B2 | 8/2013 | Cailly-Dufestel et al. |
| 8,518,438 B2 | 8/2013 | Rashid et al. |
| 8,524,267 B2 | 9/2013 | Zanella et al. |
| 8,563,038 B2 | 10/2013 | Andersen et al. |
| 8,575,196 B2 | 11/2013 | Riggs-Sauthier et al. |
| 8,591,947 B2 | 11/2013 | Vergez et al. |
| 8,597,681 B2 | 12/2013 | Park et al. |
| 8,603,514 B2 | 12/2013 | Yang et al. |
| 8,603,525 B2 | 12/2013 | Oury et al. |
| 8,609,143 B2 | 12/2013 | Fischer et al. |
| 8,617,605 B2 | 12/2013 | Fischer et al. |
| 8,623,401 B2 | 1/2014 | Modi |
| 8,623,412 B2 | 1/2014 | Farid et al. |
| 8,652,511 B2 | 2/2014 | Cottrell et al. |
| 8,653,066 B2 | 2/2014 | Bosse |
| 8,658,631 B1 | 2/2014 | Devarakonda et al. |
| 8,685,381 B2 | 4/2014 | Schlessinger et al. |
| 8,709,479 B2 | 4/2014 | Oury et al. |
| 8,722,086 B2 | 5/2014 | Arkenau-Mari et al. |
| 2001/0031278 A1 | 10/2001 | Oshlack et al. |
| 2001/0044472 A1 | 11/2001 | Upadhyay et al. |
| 2001/0046971 A1 | 11/2001 | Hammerly |
| 2002/0055512 A1 | 5/2002 | Marin et al. |
| 2002/0068718 A1 | 6/2002 | Pierce |
| 2002/0099013 A1 | 7/2002 | Piccariello et al. |
| 2002/0164373 A1 | 11/2002 | Maloney |
| 2003/0049318 A1 | 3/2003 | Davis et al. |
| 2003/0068375 A1 | 4/2003 | Wright et al. |
| 2003/0091635 A1 | 5/2003 | Baichwal et al. |
| 2003/0092724 A1 | 5/2003 | Kao et al. |
| 2003/0117622 A1 | 6/2003 | Sevick-Muraca et al. |
| 2003/0125347 A1 | 7/2003 | Anderson et al. |
| 2003/0180362 A1 | 9/2003 | Park et al. |
| 2003/0185761 A1 | 10/2003 | Dugger |
| 2003/0191147 A1 | 10/2003 | Sherman et al. |
| 2003/0199439 A1 | 10/2003 | Simon |
| 2003/0199496 A1 | 10/2003 | Simon |
| 2003/0203027 A1 | 10/2003 | Verreck et al. |
| 2003/0206898 A1 | 11/2003 | Fischkoff et al. |
| 2003/0224051 A1 | 12/2003 | Fink et al. |
| 2003/0235618 A1 | 12/2003 | Moros et al. |
| 2004/0009172 A1 | 1/2004 | Fischkoff et al. |
| 2004/0010000 A1 | 1/2004 | Ayer et al. |
| 2004/0022787 A1 | 2/2004 | Cohen et al. |
| 2004/0029864 A1 | 2/2004 | MacMillan |
| 2004/0043071 A1 | 3/2004 | Pauletti et al. |
| 2004/0062778 A1 | 4/2004 | Shefer et al. |
| 2004/0110781 A1 | 6/2004 | Harmon et al. |
| 2004/0122104 A1 | 6/2004 | Hirsh et al. |
| 2004/0156872 A1 | 8/2004 | Bosch et al. |
| 2004/0157928 A1 | 8/2004 | Kim et al. |
| 2004/0224020 A1 | 11/2004 | Schoenhard |
| 2004/0228802 A1 | 11/2004 | Chang et al. |
| 2004/0259948 A1 | 12/2004 | Tontonoz et al. |
| 2004/0265378 A1 | 12/2004 | Peng et al. |
| 2005/0004098 A1 | 1/2005 | Britten et al. |
| 2005/0013857 A1 | 1/2005 | Fu et al. |
| 2005/0020613 A1 | 1/2005 | Boehm et al. |
| 2005/0026842 A1 | 2/2005 | Simon |
| 2005/0059023 A1 | 3/2005 | Cantor |
| 2005/0106249 A1 | 5/2005 | Hwang et al. |
| 2005/0143471 A1 | 6/2005 | Gao et al. |
| 2005/0152905 A1 | 7/2005 | Omoigui |
| 2005/0169990 A1 | 8/2005 | Kao et al. |
| 2005/0222136 A1 | 10/2005 | Buschmann et al. |
| 2005/0226929 A1 | 10/2005 | Xie et al. |
| 2005/0233459 A1 | 10/2005 | Melker et al. |
| 2005/0245483 A1 | 11/2005 | Brogmann et al. |
| 2005/0265955 A1 | 12/2005 | Raman et al. |
| 2005/0266032 A1 | 12/2005 | Srinivasan et al. |
| 2005/0266072 A1 | 12/2005 | Oshlack et al. |
| 2006/0008527 A1 | 1/2006 | Lagoviyer et al. |

(56) References Cited

U.S. PATENT DOCUMENTS

| | | |
|---|---|---|
| 2006/0009478 A1 | 1/2006 | Friedmann et al. |
| 2006/0024365 A1 | 2/2006 | Vaya et al. |
| 2006/0024368 A1 | 2/2006 | Fassihi et al. |
| 2006/0039865 A1 | 2/2006 | Preston et al. |
| 2006/0052278 A1 | 3/2006 | Powell |
| 2006/0062734 A1 | 3/2006 | Melker et al. |
| 2006/0067971 A1 | 3/2006 | Story et al. |
| 2006/0073182 A1 | 4/2006 | Wong et al. |
| 2006/0074422 A1 | 4/2006 | Story et al. |
| 2006/0079557 A1 | 4/2006 | Dolle et al. |
| 2006/0093663 A1 | 5/2006 | Suzuki |
| 2006/0099254 A1 | 5/2006 | Desai et al. |
| 2006/0110327 A1 | 5/2006 | Emigh et al. |
| 2006/0111307 A1 | 5/2006 | Robbins |
| 2006/0115527 A1 | 6/2006 | Hassan et al. |
| 2006/0153915 A1 | 7/2006 | Park et al. |
| 2006/0165790 A1 | 7/2006 | Walden et al. |
| 2006/0177380 A1 | 8/2006 | Emigh et al. |
| 2006/0177381 A1 | 8/2006 | Brooks-Korn |
| 2006/0205752 A1 | 9/2006 | Whitehead |
| 2006/0210604 A1 | 9/2006 | Dadey et al. |
| 2006/0210631 A1 | 9/2006 | Patel et al. |
| 2006/0240105 A1 | 10/2006 | Devane et al. |
| 2006/0246134 A1 | 11/2006 | Venkatesh |
| 2006/0263429 A1 | 11/2006 | Feng |
| 2006/0292214 A1 | 12/2006 | Jenkins et al. |
| 2007/0003617 A1 | 1/2007 | Fischer et al. |
| 2007/0003622 A1 | 1/2007 | Srinivasan et al. |
| 2007/0009444 A1 | 1/2007 | Yamaguchi |
| 2007/0020339 A1 | 1/2007 | Bear |
| 2007/0027203 A1 | 2/2007 | Chen et al. |
| 2007/0042969 A1 | 2/2007 | Rauschkolb-Loffler et al. |
| 2007/0048228 A1 | 3/2007 | Arkenau-Maric et al. |
| 2007/0048377 A1 | 3/2007 | Rajabi-Siahboomi et al. |
| 2007/0072982 A1 | 3/2007 | Choi et al. |
| 2007/0087977 A1 | 4/2007 | Robbins |
| 2007/0104788 A1 | 5/2007 | Mulligan |
| 2007/0134493 A1 | 6/2007 | Meghpara |
| 2007/0140983 A1 | 6/2007 | Hall et al. |
| 2007/0148239 A1 | 6/2007 | Hall et al. |
| 2007/0167438 A1 | 7/2007 | Rosenzweig-Lipson |
| 2007/0190142 A1 | 8/2007 | Breitenbach et al. |
| 2007/0196491 A1 | 8/2007 | Venkatesh |
| 2007/0197661 A1 | 8/2007 | Bubnis et al. |
| 2007/0207200 A1 | 9/2007 | Plachetka et al. |
| 2007/0207222 A1 | 9/2007 | Yu et al. |
| 2007/0212417 A1 | 9/2007 | Cherukuri |
| 2007/0213717 A1 | 9/2007 | Trieu et al. |
| 2007/0213718 A1 | 9/2007 | Trieu |
| 2007/0213822 A1 | 9/2007 | Trieu |
| 2007/0213823 A1 | 9/2007 | Trieu |
| 2007/0213824 A1 | 9/2007 | Trieu |
| 2007/0215511 A1 | 9/2007 | Mehta et al. |
| 2007/0231268 A1 | 10/2007 | Emigh et al. |
| 2007/0232529 A1 | 10/2007 | Mickle et al. |
| 2007/0244093 A1 | 10/2007 | Boehm et al. |
| 2007/0249566 A1 | 10/2007 | Martin et al. |
| 2007/0254027 A1 | 11/2007 | Martin et al. |
| 2007/0281016 A1 | 12/2007 | Kao et al. |
| 2007/0281017 A1 | 12/2007 | Kao et al. |
| 2007/0281018 A1 | 12/2007 | Qiu et al. |
| 2007/0292461 A1 | 12/2007 | Tamarkin et al. |
| 2007/0292508 A1 | 12/2007 | Szamosi et al. |
| 2007/0292510 A1 | 12/2007 | Huang |
| 2007/0298103 A1 | 12/2007 | Hayes |
| 2008/0014228 A1 | 1/2008 | Darmuzey et al. |
| 2008/0014274 A1 | 1/2008 | Bubnis et al. |
| 2008/0020032 A1 | 1/2008 | Crowley et al. |
| 2008/0020039 A1 | 1/2008 | Parikh et al. |
| 2008/0026040 A1 | 1/2008 | Farr et al. |
| 2008/0026062 A1 | 1/2008 | Farr et al. |
| 2008/0031901 A1 | 2/2008 | Qiu et al. |
| 2008/0057122 A1 | 3/2008 | Toney-Parker et al. |
| 2008/0063725 A1 | 3/2008 | Guimberteau et al. |
| 2008/0069871 A1 | 3/2008 | Vaughn et al. |
| 2008/0069878 A1 | 3/2008 | Venkatesh et al. |
| 2008/0069889 A1 | 3/2008 | Cherukuri |
| 2008/0081071 A1 | 4/2008 | Sanghvi et al. |
| 2008/0085304 A1 | 4/2008 | Baichwal et al. |
| 2008/0085312 A1 | 4/2008 | Wilson et al. |
| 2008/0102113 A1 | 5/2008 | Rosenberg |
| 2008/0102123 A1 | 5/2008 | Schachter et al. |
| 2008/0103206 A1 | 5/2008 | Swann et al. |
| 2008/0132751 A1 | 6/2008 | Keller et al. |
| 2008/0152595 A1 | 6/2008 | Emigh et al. |
| 2008/0152704 A1 | 6/2008 | Bonadeo et al. |
| 2008/0171083 A1 | 7/2008 | Staniforth et al. |
| 2008/0175897 A1 | 7/2008 | Plachetka et al. |
| 2008/0193540 A1 | 8/2008 | Soula et al. |
| 2008/0207669 A1 | 8/2008 | Perez et al. |
| 2008/0226702 A1 | 9/2008 | Goldberg |
| 2008/0234237 A1 | 9/2008 | Maddaford et al. |
| 2008/0260815 A1 | 10/2008 | Hayes et al. |
| 2008/0260837 A1 | 10/2008 | Namburi et al. |
| 2008/0260844 A1 | 10/2008 | Soula et al. |
| 2008/0286343 A1 | 11/2008 | Cengic et al. |
| 2008/0286344 A1 | 11/2008 | Darmuzey et al. |
| 2008/0292683 A1 | 11/2008 | Sanghvi et al. |
| 2008/0293695 A1 | 11/2008 | Bristol et al. |
| 2008/0311162 A1 | 12/2008 | Darmuzey et al. |
| 2009/0004267 A1 | 1/2009 | Arkenau-Maric et al. |
| 2009/0004281 A1 | 1/2009 | Nghiem et al. |
| 2009/0004285 A1 | 1/2009 | Yu et al. |
| 2009/0022798 A1 | 1/2009 | Rosenberg et al. |
| 2009/0028873 A1 | 1/2009 | Gant et al. |
| 2009/0035315 A1 | 2/2009 | Christgau et al. |
| 2009/0041838 A1 | 2/2009 | Guimberteau et al. |
| 2009/0061011 A1 | 3/2009 | Talton |
| 2009/0068247 A1 | 3/2009 | Jay |
| 2009/0074866 A1 | 3/2009 | Chen |
| 2009/0081290 A1 | 3/2009 | McKenna et al. |
| 2009/0082466 A1 | 3/2009 | Babul |
| 2009/0087483 A1 | 4/2009 | Sison |
| 2009/0110724 A1 | 4/2009 | Giordano |
| 2009/0124697 A1 | 5/2009 | Cloutier et al. |
| 2009/0143761 A1 | 6/2009 | Cantor et al. |
| 2009/0155193 A1 | 6/2009 | Joabsson et al. |
| 2009/0169626 A1 | 7/2009 | Fleischer et al. |
| 2009/0175939 A1 | 7/2009 | Bosse et al. |
| 2009/0198248 A1 | 8/2009 | Yeung et al. |
| 2009/0220611 A1 | 9/2009 | Dargelas et al. |
| 2009/0220613 A1 | 9/2009 | Odidi et al. |
| 2009/0232887 A1 | 9/2009 | Odidi et al. |
| 2009/0238873 A1 | 9/2009 | Chattaraj et al. |
| 2009/0246257 A1 | 10/2009 | Modi |
| 2009/0258947 A1 | 10/2009 | Jain et al. |
| 2009/0317355 A1 | 12/2009 | Roth et al. |
| 2010/0003322 A1 | 1/2010 | Lai et al. |
| 2010/0003332 A1 | 1/2010 | Bae et al. |
| 2010/0010030 A1 | 1/2010 | Jain et al. |
| 2010/0021543 A1 | 1/2010 | Schierstedt |
| 2010/0041759 A1 | 2/2010 | Wilson et al. |
| 2010/0048602 A1 | 2/2010 | Riggs-Sauthier et al. |
| 2010/0051801 A1 | 3/2010 | Erfurth et al. |
| 2010/0076074 A1 | 3/2010 | Gant et al. |
| 2010/0080829 A1 | 4/2010 | Dulieu et al. |
| 2010/0098746 A1 | 4/2010 | King |
| 2010/0099696 A1 | 4/2010 | Soscia et al. |
| 2010/0111830 A1 | 5/2010 | Boyden et al. |
| 2010/0143449 A1 | 6/2010 | Kolesnikov |
| 2010/0152299 A1 | 6/2010 | Vasanthavada et al. |
| 2010/0172989 A1 | 7/2010 | Roth et al. |
| 2010/0196471 A1 | 8/2010 | Jain et al. |
| 2010/0196474 A1 | 8/2010 | Han et al. |
| 2010/0204259 A1 | 8/2010 | Tygesen et al. |
| 2010/0215737 A1 | 8/2010 | Coulter |
| 2010/0226943 A1 | 9/2010 | Brennan et al. |
| 2010/0226978 A1 | 9/2010 | Petereit et al. |
| 2010/0239667 A1 | 9/2010 | Hemmingsen et al. |
| 2010/0249045 A1 | 9/2010 | Babul |
| 2010/0260858 A1 | 10/2010 | Ruddy et al. |
| 2010/0266682 A1 | 10/2010 | Davar et al. |
| 2010/0286100 A1 | 11/2010 | First et al. |
| 2010/0291201 A1 | 11/2010 | Shah et al. |

(56) References Cited

U.S. PATENT DOCUMENTS

| | | |
|---|---|---|
| 2010/0291205 A1 | 11/2010 | Downie et al. |
| 2010/0304998 A1 | 12/2010 | Sem |
| 2011/0003005 A1 | 1/2011 | Venkatesh et al. |
| 2011/0003006 A1 | 1/2011 | Venkatesh et al. |
| 2011/0008424 A1 | 1/2011 | Chang et al. |
| 2011/0020440 A1 | 1/2011 | Modi et al. |
| 2011/0020451 A1 | 1/2011 | Bartholomäus et al. |
| 2011/0020776 A1 | 1/2011 | Nielsen et al. |
| 2011/0038930 A1 | 2/2011 | Barnscheid et al. |
| 2011/0052685 A1 | 3/2011 | Hou et al. |
| 2011/0077238 A1 | 3/2011 | Leech et al. |
| 2011/0091537 A1 | 4/2011 | Castan et al. |
| 2011/0091563 A1 | 4/2011 | Kurasawa et al. |
| 2011/0104214 A1 | 5/2011 | Oshlack et al. |
| 2011/0104272 A1 | 5/2011 | Hou |
| 2011/0118189 A1 | 5/2011 | Farr et al. |
| 2011/0129530 A1 | 6/2011 | Venkatesh et al. |
| 2011/0142905 A1 | 6/2011 | Bar-Shalom et al. |
| 2011/0142943 A1 | 6/2011 | Rariy et al. |
| 2011/0150989 A1 | 6/2011 | Park et al. |
| 2011/0159048 A1 | 6/2011 | Crain et al. |
| 2011/0159100 A1 | 6/2011 | Andersen et al. |
| 2011/0160239 A1 | 6/2011 | Brodbeck et al. |
| 2011/0165248 A1 | 7/2011 | Machonis |
| 2011/0182987 A1 | 7/2011 | Bawa et al. |
| 2011/0195116 A1 | 8/2011 | Hobbs et al. |
| 2011/0195520 A1 | 8/2011 | Leider et al. |
| 2011/0195989 A1 | 8/2011 | Rudnic et al. |
| 2011/0207761 A1 | 8/2011 | Losev et al. |
| 2011/0218209 A1 | 9/2011 | Yered |
| 2011/0229562 A1 | 9/2011 | Bar et al. |
| 2011/0230816 A1 | 9/2011 | Copp-Howland |
| 2011/0237614 A1 | 9/2011 | Jude-Fishburn et al. |
| 2011/0239745 A1 | 10/2011 | Satcher, Jr. et al. |
| 2011/0245208 A1 | 10/2011 | Diatchenko et al. |
| 2011/0262539 A1 | 10/2011 | Bosse et al. |
| 2011/0287095 A1 | 11/2011 | Park et al. |
| 2011/0311626 A1 | 12/2011 | Venkatesh et al. |
| 2011/0311628 A1 | 12/2011 | Muthusamy et al. |
| 2011/0311631 A1 | 12/2011 | Baer et al. |
| 2012/0009129 A1 | 1/2012 | Brzeczko |
| 2012/0010157 A1 | 1/2012 | Polvino et al. |
| 2012/0015007 A1 | 1/2012 | Bredenberg et al. |
| 2012/0015031 A1 | 1/2012 | Sesha |
| 2012/0021370 A1 | 1/2012 | Drapeau et al. |
| 2012/0022009 A1 | 1/2012 | Bryant |
| 2012/0034306 A1 | 2/2012 | Pollock et al. |
| 2012/0039957 A1 | 2/2012 | Brzeczko et al. |
| 2012/0045506 A1 | 2/2012 | Baer et al. |
| 2012/0059065 A1 | 3/2012 | Barnscheid et al. |
| 2012/0063996 A1 | 3/2012 | Bosch et al. |
| 2012/0064159 A1 | 3/2012 | Chauhan et al. |
| 2012/0065220 A1 | 3/2012 | Barnscheid et al. |
| 2012/0083506 A1 | 4/2012 | Herry et al. |
| 2012/0088786 A1 | 4/2012 | Dadagher et al. |
| 2012/0093929 A1 | 4/2012 | Oksche et al. |
| 2012/0100183 A1 | 4/2012 | Schlessinger et al. |
| 2012/0107400 A1 | 5/2012 | Muthusamy et al. |
| 2012/0121594 A1 | 5/2012 | Smith |
| 2012/0121724 A1 | 5/2012 | Maibach |
| 2012/0135075 A1 | 5/2012 | Mohammad |
| 2012/0135077 A1 | 5/2012 | Mehta et al. |
| 2012/0141554 A1 | 6/2012 | Dill |
| 2012/0164209 A1 | 6/2012 | Shah et al. |
| 2012/0164220 A1 | 6/2012 | Huang |
| 2012/0202838 A1 | 8/2012 | Ghosh et al. |
| 2012/0205532 A1 | 8/2012 | Mazza |
| 2012/0207825 A1 | 8/2012 | Roy et al. |
| 2012/0237556 A1 | 9/2012 | Schlessinger et al. |
| 2012/0245156 A1 | 9/2012 | Nguyen |
| 2012/0251590 A1 | 10/2012 | Cruz et al. |
| 2012/0282335 A1 | 11/2012 | Venkatesh et al. |
| 2012/0289534 A1 | 11/2012 | Pergolizzi et al. |
| 2012/0321674 A1 | 12/2012 | Vachon et al. |
| 2013/0004415 A1 | 1/2013 | Moudgil et al. |
| 2013/0011479 A1 | 1/2013 | Angeli et al. |
| 2013/0017262 A1 | 1/2013 | Mullen et al. |
| 2013/0022646 A1 | 1/2013 | Rudnic et al. |
| 2013/0022676 A1 | 1/2013 | Mullen et al. |
| 2013/0022677 A1 | 1/2013 | Mullen et al. |
| 2013/0023553 A1 | 1/2013 | Jude-Fishburn et al. |
| 2013/0028955 A1 | 1/2013 | Tolia |
| 2013/0028970 A1 | 1/2013 | Schwier et al. |
| 2013/0028972 A1 | 1/2013 | Schwier et al. |
| 2013/0030360 A1 | 1/2013 | Stopek et al. |
| 2013/0059010 A1 | 3/2013 | Herry et al. |
| 2013/0102959 A1 | 4/2013 | Stopek et al. |
| 2013/0115249 A1 | 5/2013 | Vergez et al. |
| 2013/0122098 A1 | 5/2013 | First et al. |
| 2013/0122101 A1 | 5/2013 | Habib et al. |
| 2013/0123294 A1 | 5/2013 | Lebon et al. |
| 2013/0129825 A1 | 5/2013 | Billoet |
| 2013/0129826 A1 | 5/2013 | Geißler et al. |
| 2013/0129828 A1 | 5/2013 | Talton |
| 2013/0136792 A1 | 5/2013 | Draper et al. |
| 2013/0156853 A1 | 6/2013 | Zhang et al. |
| 2013/0165467 A1 | 6/2013 | Hayes et al. |
| 2013/0168321 A1 | 7/2013 | Cannon et al. |
| 2013/0197021 A1 | 8/2013 | Mohammad et al. |
| 2013/0209557 A1 | 8/2013 | Barnscheid |
| 2013/0209561 A1 | 8/2013 | Kao et al. |
| 2013/0217777 A1 | 8/2013 | Kirkorian |
| 2013/0225412 A1 | 8/2013 | Sardari Lodriche et al. |
| 2013/0225625 A1 | 8/2013 | Barnscheid et al. |
| 2013/0225697 A1 | 8/2013 | Barnscheid et al. |
| 2013/0230587 A1 | 9/2013 | Pilgaonkar et al. |
| 2013/0237559 A1 | 9/2013 | Ortiz et al. |
| 2013/0245054 A1 | 9/2013 | Prater et al. |
| 2013/0259941 A1 | 10/2013 | O'Donnell |
| 2013/0273153 A1 | 10/2013 | Park et al. |
| 2013/0273162 A1 | 10/2013 | Li |
| 2013/0280176 A1 | 10/2013 | Diezi et al. |
| 2013/0280177 A1 | 10/2013 | Raman et al. |
| 2013/0280338 A1 | 10/2013 | Wening et al. |
| 2013/0303623 A1 | 11/2013 | Barnscheid et al. |
| 2013/0330409 A1 | 12/2013 | Mohammad |
| 2013/0345250 A1 | 12/2013 | Fleming |
| 2014/0010873 A1 | 1/2014 | Tygesen et al. |
| 2014/0010874 A1 | 1/2014 | Sackler |
| 2014/0017310 A1 | 1/2014 | Gower et al. |
| 2014/0031734 A1 | 1/2014 | Saxena et al. |
| 2014/0045801 A1 | 2/2014 | Rossi |
| 2014/0050787 A1 | 2/2014 | Tygesen et al. |
| 2014/0056979 A1 | 2/2014 | Huang |
| 2014/0066516 A1 | 3/2014 | Clarke et al. |
| 2014/0094438 A1 | 4/2014 | Mitchell |
| 2014/0105977 A1 | 4/2014 | Devarakonda et al. |
| 2014/0105987 A1 | 4/2014 | Rariy et al. |
| 2014/0112984 A1 | 4/2014 | Arkenau-Maric et al. |
| 2014/0112989 A1 | 4/2014 | Bartholomaus et al. |
| 2014/0127300 A1 | 5/2014 | Tengler et al. |
| 2014/0171481 A1 | 6/2014 | Liepold et al. |
| 2015/0057304 A1 | 2/2015 | Thompson et al. |
| 2015/0283087 A1 | 10/2015 | Vamvakas |

FOREIGN PATENT DOCUMENTS

| | | |
|---|---|---|
| CA | 265559 A | 11/1926 |
| CA | 2319353 A1 | 8/1999 |
| CA | 2408106 A1 | 11/2001 |
| CA | 2386794 A1 | 1/2002 |
| CA | 2544404 A1 | 6/2005 |
| CA | 2573583 A1 | 2/2006 |
| CA | 2649265 A1 | 8/2007 |
| CA | 2690829 A1 | 1/2009 |
| CA | 2737307 A1 | 4/2010 |
| CA | 2750400 A1 | 7/2010 |
| CA | 2766179 A1 | 12/2010 |
| CA | 2847613 A1 | 3/2013 |
| CN | 101824144 A | 9/2010 |
| CN | 101987081 A | 3/2011 |
| CN | 102344534 A | 2/2012 |
| CN | 102389423 A | 3/2012 |
| CN | 102648985 A | 8/2012 |

(56) References Cited

FOREIGN PATENT DOCUMENTS

| | | | |
|---|---|---|---|
| CN | 103040829 A | 4/2013 |
| CN | 103070840 A | 5/2013 |
| CN | 103637987 A | 3/2014 |
| CN | 103637998 A | 3/2014 |
| DE | 2326141 A1 | 12/1973 |
| DE | 2705051 A1 | 8/1977 |
| DE | 10215067 A1 | 10/2003 |
| DE | 10215131 A1 | 10/2003 |
| DE | 202006014131 U1 | 1/2007 |
| DE | 102007021549 A1 | 11/2008 |
| EP | 103991 A2 | 3/1984 |
| EP | 0152292 A2 | 8/1985 |
| EP | 459387 A2 | 12/1991 |
| EP | 1663229 A2 | 6/2006 |
| EP | 1980245 A1 | 10/2008 |
| EP | 2007360 A1 | 12/2008 |
| EP | 2067471 A1 | 6/2009 |
| EP | 2106799 A1 | 10/2009 |
| EP | 2123626 A1 | 11/2009 |
| EP | 2343071 A1 | 7/2011 |
| EP | 2359812 A1 | 8/2011 |
| EP | 2444064 A1 | 4/2012 |
| EP | 2457900 A1 | 5/2012 |
| EP | 2548863 A1 | 1/2013 |
| EP | 2548876 A1 | 1/2013 |
| EP | 2586607 A1 | 5/2013 |
| EP | 2626358 A1 | 8/2013 |
| FR | 2850576 A1 | 8/2004 |
| FR | 2878158 A1 | 5/2006 |
| FR | 2878161 A1 | 5/2006 |
| FR | 2892937 A1 | 5/2007 |
| FR | 2960775 A1 | 12/2011 |
| GB | 135381 A | 12/1919 |
| HU | 9903375 A2 | 2/2000 |
| IN | 2009DE00453 | 4/2003 |
| IN | 2005MU01012 | 8/2004 |
| IN | 2005MU01013 | 6/2007 |
| IN | 2006KO00351 | 7/2007 |
| JP | 55084166 | 6/1980 |
| JP | 60092214 | 5/1985 |
| JP | 11033084 | 2/1999 |
| JP | 2009256214 A | 11/2009 |
| JP | 2010053078 A | 3/2010 |
| JP | 20100173976 A | 8/2010 |
| JP | 2011256115 A | 12/2011 |
| JP | 2013249458 A | 12/2013 |
| KR | 2008026754 | 3/2008 |
| KR | 1203186 | 11/2012 |
| PL | 133984 B2 | 7/1985 |
| WO | WO-8503439 A1 | 8/1985 |
| WO | WO-9107950 A1 | 6/1991 |
| WO | WO-9324154 A1 | 12/1993 |
| WO | WO-9408551 A2 | 4/1994 |
| WO | WO-9418970 A1 | 9/1994 |
| WO | WO-9425009 A1 | 11/1994 |
| WO | WO-9426731 A1 | 11/1994 |
| WO | WO-9523591 A1 | 9/1995 |
| WO | WO-9614059 A1 | 5/1996 |
| WO | WO-9623486 A1 | 8/1996 |
| WO | WO-9704780 A2 | 2/1997 |
| WO | WO-9720556 A1 | 6/1997 |
| WO | WO-9720561 A1 | 6/1997 |
| WO | WO-97/33566 A2 | 9/1997 |
| WO | WO-9803179 A1 | 1/1998 |
| WO | WO-9907413 A1 | 2/1998 |
| WO | WO-9818610 A1 | 5/1998 |
| WO | WO-98/25613 A2 | 6/1998 |
| WO | WO-9832427 A1 | 7/1998 |
| WO | WO-9850044 A1 | 11/1998 |
| WO | WO-9850075 A1 | 11/1998 |
| WO | WO-9944591 A1 | 9/1999 |
| WO | WO-9953922 A1 | 10/1999 |
| WO | WO-9966919 A1 | 12/1999 |
| WO | WO-0021504 A1 | 4/2000 |
| WO | WO-0029022 A1 | 5/2000 |
| WO | WO-0029023 A1 | 5/2000 |
| WO | WO-0038649 A1 | 7/2000 |
| WO | WO-0061537 A2 | 10/2000 |
| WO | WO-0061541 A2 | 10/2000 |
| WO | WO-0108662 A1 | 2/2001 |
| WO | WO-0112584 A2 | 2/2001 |
| WO | WO-0115667 A1 | 3/2001 |
| WO | WO-0132101 A1 | 5/2001 |
| WO | WO-0132928 A2 | 5/2001 |
| WO | WO-0176576 A2 | 10/2001 |
| WO | WO-0185150 A2 | 11/2001 |
| WO | WO-0185257 A2 | 11/2001 |
| WO | WO-0191736 A2 | 12/2001 |
| WO | WO-0205647 A1 | 1/2002 |
| WO | WO-0232395 A2 | 4/2002 |
| WO | WO-0234237 A1 | 5/2002 |
| WO | WO-02051432 A1 | 7/2002 |
| WO | WO-02056861 A2 | 7/2002 |
| WO | WO-02100351 A2 | 12/2002 |
| WO | WO-03004009 A1 | 1/2003 |
| WO | WO-03013481 A1 | 2/2003 |
| WO | WO-03020200 A2 | 3/2003 |
| WO | WO-03024430 A1 | 3/2003 |
| WO | WO-03032990 A2 | 4/2003 |
| WO | WO-03034991 A2 | 5/2003 |
| WO | WO-03051878 A1 | 6/2003 |
| WO | WO-03063834 A1 | 8/2003 |
| WO | WO-03065988 A2 | 8/2003 |
| WO | WO-03066029 A2 | 8/2003 |
| WO | WO-03066030 A2 | 8/2003 |
| WO | WO-03068197 A1 | 8/2003 |
| WO | WO-03079972 A2 | 10/2003 |
| WO | WO-03088991 A1 | 10/2003 |
| WO | WO-03092648 A1 | 11/2003 |
| WO | WO-03101476 A1 | 12/2003 |
| WO | WO-2004026256 A2 | 4/2004 |
| WO | WO-2004039320 A2 | 5/2004 |
| WO | WO-2004045551 A2 | 6/2004 |
| WO | WO-2004054542 A2 | 7/2004 |
| WO | WO-2004064832 A2 | 8/2004 |
| WO | WO-2004069135 A2 | 8/2004 |
| WO | WO-2004062719 A1 | 9/2004 |
| WO | WO-2004075832 A2 | 9/2004 |
| WO | WO-2004082588 A2 | 9/2004 |
| WO | WO-2004084868 A1 | 10/2004 |
| WO | WO-2004108163 A1 | 12/2004 |
| WO | WO-2005000310 A1 | 1/2005 |
| WO | WO-2005000331 A2 | 1/2005 |
| WO | WO-2005002597 A1 | 1/2005 |
| WO | WO-2005004989 A2 | 1/2005 |
| WO | WO-2005009409 A2 | 2/2005 |
| WO | WO-2005028539 A2 | 3/2005 |
| WO | WO-2005030181 A1 | 4/2005 |
| WO | WO-2005030182 A1 | 4/2005 |
| WO | WO-2005032474 A2 | 4/2005 |
| WO | WO-2005032555 A2 | 4/2005 |
| WO | WO-2005038049 A2 | 4/2005 |
| WO | WO-2005046727 A2 | 5/2005 |
| WO | WO-2005051356 A1 | 6/2005 |
| WO | WO-2005058303 A1 | 6/2005 |
| WO | WO-2005063206 A1 | 7/2005 |
| WO | WO-2005063219 A2 | 7/2005 |
| WO | WO-2005079760 A1 | 9/2005 |
| WO | WO-2005092306 A1 | 10/2005 |
| WO | WO-2005102338 A1 | 11/2005 |
| WO | WO-2005103070 A1 | 11/2005 |
| WO | WO-2005107467 A2 | 11/2005 |
| WO | WO-2005107726 A2 | 11/2005 |
| WO | WO-2005123192 A2 | 12/2005 |
| WO | WO-2005123193 A2 | 12/2005 |
| WO | WO-2006014967 A1 | 2/2006 |
| WO | WO-2006020930 A2 | 2/2006 |
| WO | WO-2006024018 A2 | 3/2006 |
| WO | WO-2006024881 A2 | 3/2006 |
| WO | WO-2006030402 A2 | 3/2006 |
| WO | WO-2006046114 A2 | 5/2006 |
| WO | WO-2006050165 A2 | 5/2006 |
| WO | WO-2006069030 A1 | 6/2006 |
| WO | WO-2006069202 A2 | 6/2006 |

(56) References Cited

FOREIGN PATENT DOCUMENTS

| | | |
|---|---|---|
| WO | WO-2006075123 A1 | 7/2006 |
| WO | WO-2005070465 A2 | 8/2006 |
| WO | WO-2006085101 A2 | 8/2006 |
| WO | WO-2006092691 A1 | 9/2006 |
| WO | WO-2006099541 A2 | 9/2006 |
| WO | WO-2006103418 A1 | 10/2006 |
| WO | WO-2006103551 A1 | 10/2006 |
| WO | WO-2006105205 A1 | 10/2006 |
| WO | WO-2006116148 A2 | 11/2006 |
| WO | WO-2006133733 A1 | 12/2006 |
| WO | WO-2006138278 A1 | 12/2006 |
| WO | WO-2007021970 A2 | 2/2007 |
| WO | WO-2007036671 A2 | 4/2007 |
| WO | WO-2007050631 A2 | 5/2007 |
| WO | WO-2007056142 A2 | 5/2007 |
| WO | WO-2007058960 A1 | 5/2007 |
| WO | WO-2007070632 A2 | 6/2007 |
| WO | WO-2007072503 A2 | 6/2007 |
| WO | WO-2007087452 A2 | 8/2007 |
| WO | WO-2007089328 A2 | 8/2007 |
| WO | WO-2007094694 A1 | 8/2007 |
| WO | WO-2007106550 A2 | 9/2007 |
| WO | WO-2007128349 A1 | 11/2007 |
| WO | WO-2007128884 A1 | 11/2007 |
| WO | WO-2007131357 A1 | 11/2007 |
| WO | WO-2007133583 A2 | 11/2007 |
| WO | WO-2007135193 A2 | 11/2007 |
| WO | WO-2007141328 A1 | 12/2007 |
| WO | WO-2007149438 A2 | 12/2007 |
| WO | WO-2008001341 A1 | 1/2008 |
| WO | WO-2008007152 A2 | 1/2008 |
| WO | WO-2008008364 A2 | 1/2008 |
| WO | WO-2008011169 A2 | 1/2008 |
| WO | WO-2008013710 A2 | 1/2008 |
| WO | WO-2008/021394 A2 | 2/2008 |
| WO | WO-2008023261 A1 | 2/2008 |
| WO | WO-2008027350 A2 | 3/2008 |
| WO | WO-2008027442 A2 | 3/2008 |
| WO | WO-2008033351 A2 | 3/2008 |
| WO | WO-2008033523 A1 | 3/2008 |
| WO | WO-2008057579 A2 | 5/2008 |
| WO | WO-2008057608 A2 | 5/2008 |
| WO | WO-2008060552 A2 | 5/2008 |
| WO | WO-2008063625 A2 | 5/2008 |
| WO | WO-2008067222 A1 | 6/2008 |
| WO | WO-2008068471 A1 | 6/2008 |
| WO | WO-2008070268 A2 | 6/2008 |
| WO | WO-2008086804 A2 | 7/2008 |
| WO | WO-2008097976 A1 | 8/2008 |
| WO | WO-2008100977 A2 | 8/2008 |
| WO | WO-2008106429 A2 | 9/2008 |
| WO | WO-2008107410 A1 | 9/2008 |
| WO | WO-2008108957 A2 | 9/2008 |
| WO | WO-2008108958 A2 | 9/2008 |
| WO | WO-2008108986 A2 | 9/2008 |
| WO | WO-2008131056 A2 | 10/2008 |
| WO | WO-2008131057 A2 | 10/2008 |
| WO | WO-2008132712 A2 | 11/2008 |
| WO | WO-2008133928 A2 | 11/2008 |
| WO | WO-2008134600 A1 | 11/2008 |
| WO | WO-2008135283 A1 | 11/2008 |
| WO | WO-2008140459 A1 | 11/2008 |
| WO | WO-2008140460 A1 | 11/2008 |
| WO | WO-2008140461 A1 | 11/2008 |
| WO | WO-2008141189 A1 | 11/2008 |
| WO | WO-2008148798 A2 | 12/2008 |
| WO | WO-2008155620 A1 | 12/2008 |
| WO | WO-2008157308 A2 | 12/2008 |
| WO | WO-2009002299 A1 | 12/2008 |
| WO | WO-2009005613 A2 | 1/2009 |
| WO | WO-2009005803 A1 | 1/2009 |
| WO | WO-2009014534 A1 | 1/2009 |
| WO | WO-2009021055 A1 | 2/2009 |
| WO | WO-2009023672 A2 | 2/2009 |
| WO | WO-2009026241 A1 | 2/2009 |
| WO | WO-2009042960 A1 | 4/2009 |
| WO | WO-2009047175 A2 | 4/2009 |
| WO | WO-2009073686 A1 | 6/2009 |
| WO | WO-2009076361 A1 | 6/2009 |
| WO | WO-2009076764 A1 | 6/2009 |
| WO | WO-2009089134 A1 | 7/2009 |
| WO | WO-2009100118 A1 | 8/2009 |
| WO | WO-2009104838 A1 | 8/2009 |
| WO | WO-2009109911 A1 | 9/2009 |
| WO | WO-2009114648 A1 | 9/2009 |
| WO | WO-2009118764 A1 | 10/2009 |
| WO | WO-2009120889 A2 | 10/2009 |
| WO | WO-2009121496 A2 | 10/2009 |
| WO | WO-2009124755 A1 | 10/2009 |
| WO | WO-2009126931 A2 | 10/2009 |
| WO | WO-2009/137086 A1 | 11/2009 |
| WO | WO-2009134336 A1 | 11/2009 |
| WO | WO-2009143295 A1 | 11/2009 |
| WO | WO-2009143299 A1 | 11/2009 |
| WO | WO-2009/152133 A1 | 12/2009 |
| WO | WO-2010000073 A1 | 1/2010 |
| WO | WO-2010017821 A1 | 2/2010 |
| WO | WO-2010032128 A1 | 3/2010 |
| WO | WO-2010033195 A1 | 3/2010 |
| WO | WO-2010068789 A1 | 6/2010 |
| WO | WO-2010069050 A1 | 6/2010 |
| WO | WO-2010083894 A1 | 7/2010 |
| WO | WO-2010089132 A1 | 8/2010 |
| WO | WO-2010096045 A1 | 8/2010 |
| WO | WO-2010103365 A2 | 9/2010 |
| WO | WO-2010103367 A1 | 9/2010 |
| WO | WO-2010123999 A2 | 10/2010 |
| WO | WO-2010124089 A2 | 10/2010 |
| WO | WO-2010127345 A2 | 11/2010 |
| WO | WO-2010127346 A1 | 11/2010 |
| WO | WO-2010132095 A1 | 11/2010 |
| WO | WO-2010135340 A2 | 11/2010 |
| WO | WO-2010140007 A2 | 12/2010 |
| WO | WO-2010141505 A1 | 12/2010 |
| WO | WO-2010150930 A1 | 12/2010 |
| WO | WO-2010151020 A2 | 12/2010 |
| WO | WO-2010151823 A1 | 12/2010 |
| WO | WO-2011005671 A1 | 1/2011 |
| WO | WO-2011006012 A1 | 1/2011 |
| WO | WO-2011008298 A2 | 1/2011 |
| WO | WO-2011009603 A1 | 1/2011 |
| WO | WO-2011009604 A1 | 1/2011 |
| WO | WO-2011011060 A1 | 1/2011 |
| WO | WO-2011011199 A1 | 1/2011 |
| WO | WO-2011011543 A1 | 1/2011 |
| WO | WO-2011012715 A1 | 2/2011 |
| WO | WO-2011039768 A2 | 4/2011 |
| WO | WO-2011045769 A2 | 4/2011 |
| WO | WO-2011057199 A1 | 5/2011 |
| WO | WO-2011066287 A1 | 6/2011 |
| WO | WO-2011066980 A2 | 6/2011 |
| WO | WO-2011068723 A1 | 6/2011 |
| WO | WO-2011068881 A1 | 6/2011 |
| WO | WO-2011084593 A2 | 7/2011 |
| WO | WO-2011086193 A1 | 7/2011 |
| WO | WO-2011088140 A1 | 7/2011 |
| WO | WO-2011106076 A1 | 9/2011 |
| WO | WO-2011107750 A2 | 9/2011 |
| WO | WO-2011107855 A2 | 9/2011 |
| WO | WO-2011120084 A1 | 10/2011 |
| WO | WO-2011123719 A2 | 10/2011 |
| WO | WO-2011123866 A1 | 10/2011 |
| WO | WO-2011127467 A1 | 10/2011 |
| WO | WO-2011139595 A2 | 11/2011 |
| WO | WO-2012007159 A2 | 1/2012 |
| WO | WO-2012011917 A1 | 1/2012 |
| WO | WO-2012016569 A2 | 2/2012 |
| WO | WO-2012020097 A2 | 2/2012 |
| WO | WO-2012021819 A1 | 2/2012 |
| WO | WO-2012028319 A1 | 3/2012 |
| WO | WO-2012037457 A1 | 3/2012 |
| WO | WO-2012052955 A1 | 4/2012 |
| WO | WO-2012054071 A1 | 4/2012 |
| WO | WO-2012054831 A2 | 4/2012 |

(56) References Cited

FOREIGN PATENT DOCUMENTS

| | | |
|---|---|---|
| WO | WO-2012061779 A1 | 5/2012 |
| WO | WO-2012063257 A2 | 5/2012 |
| WO | WO-2012069175 A1 | 5/2012 |
| WO | WO-2012076907 A2 | 6/2012 |
| WO | WO-2012077110 A2 | 6/2012 |
| WO | WO-2012085236 A1 | 6/2012 |
| WO | WO-2012085656 A2 | 6/2012 |
| WO | WO-2012085657 A2 | 6/2012 |
| WO | WO-2012087377 A1 | 6/2012 |
| WO | WO-2012098281 A2 | 7/2012 |
| WO | WO-2012106343 A2 | 8/2012 |
| WO | WO-2012112933 A1 | 8/2012 |
| WO | WO-2012112952 A1 | 8/2012 |
| WO | WO-2012116278 A1 | 8/2012 |
| WO | WO-2012116279 A1 | 8/2012 |
| WO | WO-2012121461 A1 | 9/2012 |
| WO | WO-2012127506 A1 | 9/2012 |
| WO | WO-2012131463 A2 | 10/2012 |
| WO | WO-2012139191 A1 | 10/2012 |
| WO | WO-2012177986 A2 | 12/2012 |
| WO | WO-2013000578 A1 | 1/2013 |
| WO | WO-2013003845 A1 | 1/2013 |
| WO | WO-2013010880 A1 | 1/2013 |
| WO | WO-2013010881 A1 | 1/2013 |
| WO | WO-2013015545 A1 | 1/2013 |
| WO | WO-2013038267 A1 | 3/2013 |
| WO | WO-2013038268 A1 | 3/2013 |
| WO | WO-2013050539 A2 | 4/2013 |
| WO | WO-2013057570 A2 | 4/2013 |
| WO | WO-2013058496 A1 | 4/2013 |
| WO | WO-2013059805 A1 | 4/2013 |
| WO | WO-2013061161 A2 | 5/2013 |
| WO | WO-2013070617 A1 | 5/2013 |
| WO | WO-2013072395 A1 | 5/2013 |
| WO | WO-2013077851 A1 | 5/2013 |
| WO | WO-2013082308 A1 | 6/2013 |
| WO | WO-2013083710 A1 | 6/2013 |
| WO | WO-2013084059 A1 | 6/2013 |
| WO | WO-2013093877 A2 | 6/2013 |
| WO | WO-2013103537 A1 | 7/2013 |
| WO | WO-2013119231 A1 | 8/2013 |
| WO | WO-2013128276 A2 | 9/2013 |
| WO | WO-2013128447 A1 | 9/2013 |
| WO | WO-2013136078 A1 | 9/2013 |
| WO | WO-2013138118 A1 | 9/2013 |
| WO | WO-2013151638 A1 | 10/2013 |
| WO | WO-2013155430 A1 | 10/2013 |
| WO | WO-2013158810 A1 | 10/2013 |
| WO | WO-2013158814 A1 | 10/2013 |
| WO | WO-2013170052 A1 | 11/2013 |
| WO | WO-2013171146 A1 | 11/2013 |
| WO | WO-2013175511 A1 | 11/2013 |
| WO | WO-2014001268 A1 | 1/2014 |
| WO | WO-2014001904 A1 | 1/2014 |
| WO | WO-2014001905 A1 | 1/2014 |
| WO | WO-2014006004 A1 | 1/2014 |
| WO | WO-2014011830 A1 | 1/2014 |
| WO | WO-2014025638 A1 | 2/2014 |
| WO | WO-2014045305 A1 | 3/2014 |
| WO | WO-2014047731 A1 | 4/2014 |
| WO | WO-2014059512 A1 | 4/2014 |
| WO | WO-2015023675 A2 | 2/2015 |
| WO | WO-2015023704 A1 | 2/2015 |

OTHER PUBLICATIONS

Soininen et al., "Dissolution rate of different kinds of granulated micronized paracetamol with adjuvant incorporated either inter- or intragranularly", Acta Pharmaceutica Fennica, 1981, vol. 90, No. 2, pp. 153-162.

Sako et al., "Relationship between gelation rate of controlled-release acetaminophen tablets containing polyethylene bride and colonic drug release in dogs", Pharmaceutical Research, 1996, vol. 13, No. 4, pp, 594-598.

Djuris et at, "Application of quality by design concepts in the development of fluidized bed granulation and tableting processes", Journal of Pharmaceutical Sciences, 2013, vol. 102, No. 6, pp. 1869-1882.

Dahl et al., "Mechanisms to control drug release from pellets coated with a silicone elastomer aqueous dispersion", Pharmaceutical Research, 1992, vol. 9, No. 3, pp. 398-405.

Sako, et al., "Influence of water soluble fillers in hydroxypropylmethylcellulose matrices on in vitro and in vivo drug release", Journal of Controlled Release, 2002, vol. 81, No. 1-2, pp, 165-172.

Borini et al., "Hot melt granulation of coarse pharmaceutical powders in a spouted bed", Powder Technology, 2009, vol. 189. No. 3, pp. 520-527.

Gohel et al., "Fabrication and Evaluation of Bi-layer Tablet Containing Conventional Paracetamol and Modified Release Diclofenac Sodium", Indian J. Pharm Sci., 2010, vol. 72, No. 2. pp. 191-196.

Stambaugh et al., "Double-blind, randomized comparison of the analgesic and pharmacokinetic profiles of controlled- and immediate-release oral oxycodone in cancer pain patients", 2001, vol. 41, No. 5, pp. 500-506.

Sunshine et al., "Analgesic Efficacy of Controlled-Release Oxycodone in Postoperative Pain", Journal of Clinical Pharmacology, 1996, vol. 36, No. 7, pp. 595-603.

Harris, et al., "Abuse potential, pharmacokinetics, pharmacodynamics, and safety of intranasally administered crushed oxycodone HCl abuse-deterrent controlled-release tablets in recreational opioid users", Journal of Clinical Pharmacology, 2014, vol. 54, No. 4, pp. 468-477.

Gosai et al., "Bioequivalence of oxycodone hydrochoride extended release tablets to marketed reference products OxyContin® in Canada and US", Int J Clin Pharmacol Ther., 2013, vol. 51, No. 11, pp. 895-907.

Upadhye et al., "Polyethylene Oxide and Ethylcellulose for Tamper Resistance and Controlled Drug Delivery", Melt Extrusion, AAPS Advances in the Pharmaceutical Sciences Series, 2013, vol. 9, pp. 145-158.

Benziger et al., "Differential Effects of Food on the Bioavailability of Controlled-Release Oxycodone Tablets and Immediate-Release Oxycodone Solution", Journal of Pharmaceutical Sciences. vol. 85, No. 4, pp. 407-410.

International Search Report for International Application No. PCT/US14/50737; International Filing Date Aug. 12, 2014.

Bartholomaus et al., "New Abuse Deterrent Formulation (ADP) Technology for Immediate-Release Opioids". Drug Development & Delivery, 2013, vol. 13, No. 8, pp. 76-81.

International Search Report for International Application PCT/US2015/039336; Filing Date Jul. 7, 2015.

MP Biomedicals. Lecithin Meiting Point Properties. Retrieved Feb. 2016.

"Poloxamer", from Wikipedia, the free encyclopedia—4 Pages.

IMMEDIATE RELEASE ABUSE DETERRENT LIQUID FILL DOSAGE FORM

CROSS REFERENCE TO RELATED APPLICATIONS

This application claims priority to U.S. Provisional Application No. 62/025,878 filed Jul. 17, 2014, the disclosure of which is incorporated herein by reference in their entirety.

FIELD OF THE TECHNOLOGY

The present disclosure relates to an oral immediate release, abuse deterrent dosage form. The dosage form contains polyethylene glycol (PEG) to reduce abuse by non-oral administration routes, e.g. intranasal and/or intravenous. The composition of PEG is designed to allow for immediate release of the active ingredient while deterring abuse and maintaining stability of the dosage form at elevated temperatures.

BACKGROUND

FDA-approved drugs are provided in many different forms based on the type of active substance, the indication treated and the preferred route of administration. These forms include enteral formulations (e.g., tablets, capsules or pills), parenteral formulations (e.g., injectable formulations such as intravenous, subcutaneous, intramuscular and intraarticular), liquid formulations (e.g., elixirs), lyophilized formulations and topical formulations. A majority of the FDA-approved drugs are currently available in enteral form, as either a tablet or capsule.

Several formulations have been investigated for deterring abuse, either by oral ingestion of the drug with alcohol, or by non-oral administration routes such as intranasal and/or intravenous administration. For example, U.S. 2014/0010873 (assigned to Egalet Ltd.) is directed to an abuse-deterrent pharmaceutical composition including at least one polyethylene oxide and at least one plasticizer. The polyethylene oxide has an average molecular weight of at least 1,000,000 Daltons, and the pharmaceutical composition includes at least 5 percent w/w of the at least one plasticizer. The pharmaceutical composition is designed to prevent immediate release of the at least one active drug substance after physical tampering. U.S. 2009/0123386 (assigned to MW Encap Limited) is directed to an abuse deterrent capsule including at least one modifier selected to prevent abuse. The modifier may have a high melting point or be insoluble in aqueous solvents or ethanol. For example, the high melting point excipient may be Poloxamer 188 or PEG 8000. U.S. 2010/0204259 (assigned to Egalet A/S) is directed to immediate release pharmaceutical compositions that are resistant to abuse by intake of alcohol. The release of the drug substance from the immediate release composition is decreased when the composition is exposed to a dissolution medium that includes ethanol. The compositions may be formulated to include at least one polyglycol and at least one effervescent agent.

SUMMARY

The present disclosure relates to an immediate release, abuse deterrent capsule including an active substance susceptible to abuse, a first polyethylene glycol (PEG) having an average molecular weight between about 30,000 Daltons and about 40,000 Daltons; and a second PEG having an average molecular weight between about 3000 Daltons and about 4000 Daltons. The ratio of the first PEG to the second PEG is less than about 1:4 w/w.

In some embodiments, the first PEG and the second PEG together are at least about 60 wt % of the dosage form. In some embodiments, the active substance is hydrocodone bitartrate. In other embodiments, the active substance is oxycodone hydrochloride (HCl). In some embodiments the capsule includes a grey dye including FD&C Blue #1, FD&C Yellow #6, and FD&C Red #40. In certain embodiments, the dye reduces abuse by providing a visual deterrent to injecting. In certain embodiments, about 60%, 70% 75%, 80%. 85% or about 90% or more of the capsule fill contents are soluble in both water and/or alcohol, e.g., ethanol. In certain embodiments, the ratio of the first PEG to the second PEG is between about 1:7 w/w and about 1:11 w/w. In some embodiments, the first PEG has an average molecular weight of about 35,000 Daltons and the second PEG has an average molecular weight of about 3350 Daltons. In some embodiments, the capsule includes at least about 2.5 wt % of the active substance. The capsule may be prepared by filling a capsule body with a heated homogenized suspension including the active substance, the first PEG and the second PEG.

The present disclosure also relates to an immediate release, abuse deterrent capsule including an active substance susceptible to abuse and polyethylene glycol with a weighted average molecular weight between about 6200 Daltons and about 7800 Daltons. In certain embodiments, the capsule includes at least about 60 wt % of PEG. In some embodiments, the active substance is hydrocodone bitartrate. In other embodiments, the active substance is oxycodone HCl.

The present disclosure also relates to an immediate release, abuse deterrent capsule including an active substance susceptible to abuse, a first PEG having a melting point greater than or equal to about 60° C., and a second PEG having a melting point less than or equal to about 57° C. The contents of the capsule can be solid at 40° C./75% relative humidity. In some embodiments, at least 90% of the active ingredient can be released from the capsule within 30 minutes following administration or via dissolution testing. In other embodiments, at least 75% of the active ingredients can be released from the capsule within 45 minutes following administration or via dissolution testing. In some embodiments, the first PEG and the second PEG together are at least about 60 wt % of the capsule. In particular embodiments, the active substance is hydrocodone bitartrate. In other embodiments, the active substance is oxycodone HCl.

The present disclosure also relates to a process for the production of an immediate release, abuse deterrent capsule including at least one active substance susceptible to abuse including preparing a homogenized suspension of the at least one active substance susceptible to abuse, a first PEG having an average molecular weight between about 30,000 Daltons and about 40,000 Daltons, and a second PEG having an average molecular weight between about 3000 Daltons and about 4000 Daltons. The process can further include filling the homogenized suspension into a capsule body to produce an encapsulated dosage form. The ratio of the first PEG to the second PEG can be less than about 1:4 w/w, e.g., between about 1:7 w/w and about 1:11 w/w.

In certain embodiments of the aforementioned process, the first PEG and the second PEG together can be at least about 60 wt % of the capsule. In particular embodiments, the active substance is hydrocodone bitartrate. In other embodiments, the active substance is oxycodone HCl. In certain embodiments the capsule can be formed by joining a capsule body with a capsule cap.

The present disclosure also relates to a method of treating pain including administering to a subject in need thereof a therapeutically effective amount of any of the aforementioned capsules.

BRIEF DESCRIPTION OF THE DRAWINGS

The foregoing and other advantages provided by the present disclosure will be more fully understood from the following description of exemplary embodiments when read together with the accompanying drawings, in which.

DETAILED DESCRIPTION

Figure 1:
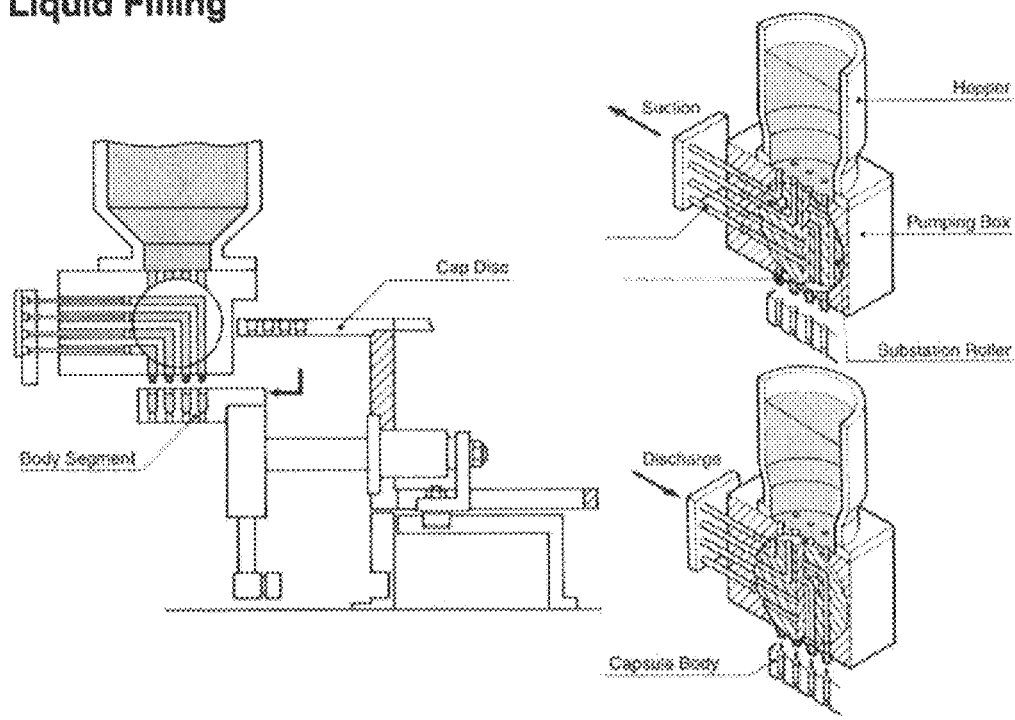
FIG. 1 shows cross sections of a capsule filling machine including the body segment, the cap disc, the hopper, the pumping box, the substation roller, and capsule bodies.

Abuse of prescription drugs, particularly opioids, is a serious and growing public health concern. To address this concern, new formulations are being developed that contain abuse-deterrent properties. Abuse deterrent properties include properties that make product manipulation more difficult or make abuse of the manipulated product less attractive or rewarding.

Recently the FDA issued a draft guidance for industry related to formulations having abuse deterrent properties. *Guidance for Industry: Abuse Deterrent Opioids—Evaluation and Labeling*, U.S. Department of Health and Human Services, FDA, CDER, January 2013, the entire contents of which are incorporated herein by reference. These guidelines separate abuse deterrent formulations into six categories, including: physical/chemical barriers, agonist/antagonist combinations, aversion, delivery system, prodrug, or a combination of the aforementioned. As described by the FDA guidance, the categories are:

Physical/Chemical barriers—Physical barriers can prevent chewing, pulverizing, cutting, grating, or grinding. Chemical barriers can resist extraction of the opioid using common solvents like water, alcohol, or other organic solvents. Physical and chemical barriers can change the physical form of an oral drug rendering it less amenable to abuse.

Agonist/Antagonist combinations—An opioid antagonist can be added to interfere with, reduce, or defeat the euphoria associated with abuse. The antagonist can be sequestered and released only upon manipulation of the product. For example, a drug product may be formulated such that the substance that acts as an antagonist is not clinically active when the product is swallowed but becomes active if the product is crushed and injected or snorted.

Aversion—Substances can be combined to produce an unpleasant effect if the dosage form is manipulated prior to ingestion or a higher dosage than directed is used.

Delivery System (including depot injectable formulations and implants)—Certain drug release designs or the method of drug delivery can offer resistance to abuse. For example, a sustained-release depot injectable formulation that is administered intramuscularly or a subcutaneous implant can be more difficult to manipulate.

Prodrug—A prodrug that lacks opioid activity until transformed in the gastrointestinal tract can be unattractive for intravenous injection or intranasal routes of abuse.

Combination—Two or more of the above methods can be combined to deter abuse.

An opioid analgesic submitted for abuse deterrent formulation (ADF) labeling must show conformance to one or more of these categories. The present disclosure relates to an abuse deterrent dosage form for oral administration, which provides immediate release of an active pharmaceutical substance and conforms to one or more of these categories. In one embodiment, the abuse deterrent dosage form of the present disclosure conforms to at least one of the six FDA categories. In another embodiment, the abuse deterrent dosage form of the present disclosure conforms to at least two of the six FDA categories. In another embodiment, the abuse deterrent dosage form of the present disclosure conforms to at least three of the six FDA categories. In another embodiment, the abuse deterrent dosage form of the present disclosure conforms to at least four of the six FDA categories. In another embodiment, the abuse deterrent dosage form of the present disclosure conforms to at least five of the six FDA categories.

For example, an abuse deterrent dosage form of the present disclosure can reduce abuse by the incorporation of at least one physical barrier. The physical barrier is designed to prevent abuse based on chewing, pulverizing, cutting, grating or grinding. Preferably, the physical barrier prevents or reduces the effectiveness of these methods. As used herein, the phrase "abuse deterrent" means that the active substance cannot readily be separated from the formulation in a form suitable for abuse by such means as, for example, grinding. The abuse deterrent form of the present disclosure cannot be easily ground, extracted from, or both. Abuse deterrent measures render it difficult to transform the dosage form into a residue or extract for non-oral administration, such as intranasal or intravenous.

In one embodiment, the present disclosure relates to an oral, immediate release, abuse deterrent dosage form including an active substance susceptible to abuse, a first PEG having an average molecular weight between about 30.000 Daltons and about 40,000 Daltons, and a second PEG having an average molecular weight between about 3000 Daltons and about 4000 Daltons. The ratio of the first PEG to the second PEG can be less than about 1:4 w/w. The wt % of active substance in the formulation may also vary depending on the active substance of the dosage form. In some embodiments, the dosage form includes at least about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, 1.5 wt %, 2 wt %, 2.5 wt %, 3 wt %, 4 wt %, 5 wt %, 6 wt %, 7 wt %, 7.5 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %. 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt %, 60 wt %, 65 wt %, 69 wt %, 70 wt %, 75 wt %, 80 wt %, 85 wt %, 88 wt %, 90 wt %, or 95 wt % of the active substance. Any of these values may be used to define a range for the wt % of the active substance depending on the application. For example, the amount of active substance in the dosage form may range from about 0.10 wt % to about 60 wt %. Particularly, the amount of active substance in the dosage form may range from about 0.1 wt % to about 1.5 wt %, from about 5 wt % to about 30 wt %, from about 15 wt % to about 20 wt %, from about 15 wt % to about 30 wt %, from about 40 wt % to about 60 wt %, from about 40 wt % to about 50 wt %, or from about 42 wt % to about 46 wt %.

For example, the dosage form may be a 100 mg capsule including about 5 mg, about 10 mg, about 15 mg, about 20 mg, or about 30 mg of active substance (e.g., oxycodone HCl). In other embodiments, the dosage form may be a 150 mg capsule including about 5 mg, about 10 mg, about 15 mg, about 20 mg, about 30 mg, or about 45 mg of active substance (e.g., oxycodone HCl). In other embodiments, the dosage form may be a 200 mg capsule including about 5 mg, about 10 mg, about 15 mg, about 20 mg, about 30 mg, about 40 mg, about 50 mg, or about 60 mg of active substance (e.g., oxycodone HCl). In other embodiments, the dosage form may be a 700 mg capsule including about 2.5 mg, about 5 mg, about 7.5 mg, about 10 mg, about 15 mg, about 20 mg, about 30 mg, about 45 mg, about 50 mg, about 60 mg, about 70 mg, about 80 mg, about 90 mg or about 100 mg of an active substance (e.g., hydrocodone bitartrate).

As used herein, the term "active" or "active substance" or "active substance susceptible to abuse" or "API" means any opioid or opioid related compound subject to potential abuse. The active substance may include, without limitation, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levophenacylmorphan, levorphanol, lofentanil, meperidine, meptazinol, metazocine, methadone, metopon, morphine, myrophine, nalbulphine, narceine, nicomorphine, norpipanone, opium, oxycodone, papvretum, pentazocine, phenadoxone, phenazocine, phenomorphan, phenoperidine, piminodine, propiram, propoxyphene, sufentanil, tilidine, tapentadol, and tramadol, and pharmaceutically acceptable salts and mixtures thereof. For example, in some embodiments the active can be oxycodone HCl or hydrocodone bitartrate. In the dosage forms of the present disclosure, the active substance is not oxymorphone.

In particular, the active substance can be hydrocodone bitartrate or oxycodone HCl. The dosage form of the present disclosure can be rendered abuse deterrent by incorporating PEG in the dosage form. The PEG can deter abuse by preventing at least 50%, or at least 75%, of the capsule weight from being ground to a particle size below 500 μm, such as after 30 seconds of milling at 10,000 RPM. PEG can also prevent extraction of the active substance from the dosage form using an alcohol. Abusers can use the partial solubility characteristics of dosage form excipients to extract the active substance using alcohol and subsequently burn off the alcohol to form a purer residue containing the active substance. The inclusion of PEG in the formulation can prevent or reduce extraction because PEG can melt and form a wax before the alcohol can be completely evaporated or flashed off, an abuser may not be able to obtain a residue containing the active substance. Addition of a dye to the dosage form can also result in a colored solution after extraction of the active substance, deterring intravenous injection. By selecting the appropriate average molecular weight and quantity of PEG present within a dosage form, the characteristics of the dosage form can be manipulated in a way to create a wide array of abuse deterrent capsules having immediate release profiles.

Inclusion of PEG in the dosage form can result in the inability of the dosage form, e.g., capsule, to be abused by pulverizing and snorting, pulverizing and injecting, or combinations thereof. For example, the abuse deterrent dosage form of the present disclosure may be incapable of being significantly pulverized by physical or mechanical force due at least in part to the waxy characteristics of the PEG.

One of the most common means of abuse of an orally administered opioid analgesic involves the manipulation of the oral dosage form in order to cause rapid delivery to the bloodstream via nasal insufflation. In order for insufflation to be used as an effective means of abuse, the original dosage form must be manipulated so as to decrease the particle size of the ingested drug to about 500 μm or less. A particle size of about 500 μm or less is necessary for effective intranasal absorption to occur. By limiting the quantity of particles under about 500 μm that an abuser can obtain by reasonable methods, one can render insufflation ineffective as a means of abuse. Thus one way to prevent abuse by nasal insufflation is by capturing the active substance susceptible to abuse in a matrix which is resistant to being physically broken down to produce particles smaller than about 500 μm.

The dosage form of the present disclosure can inhibit manipulation by grinding or pulverizing using common equipment, such as a coffee grinder. For example, the formulation can deter abuse by limiting the particle size to which the formulation may be ground. The formulation prevents the dosage form, or at least substantial portions of the dosage from, from being ground in particles having a particle size of about 500 μm or less that may pass through the mucus membranes of the nasal cavity. The dosage form can also significantly limit the extraction of the active substance by common solvents (e.g., cold water or distilled aqueous ethanol) from the formulation. For example, the formulation deters abuse by limiting the ability of persons to extract the active substance from the formulation (either intentionally or unintentionally), such that the active substance cannot easily be concentrated for parenteral administration. The abuse deterrent dosage form may also include, but does not require, the incorporation of other deterrents such as antagonists or irritants.

For example, in one embodiment, the abuse deterrent can work as follows. If the dosage form is extracted with alcohol or an aqueous solution, the PEG and/or dye will also be extracted and cannot easily be separated from the active substance, preventing the preparation of pure drug for intravenous administration. Extraction with a solution would result in a grey/black liquid containing the PEG, dye and active substance. The inclusion of PEG in the formulation can prevent or reduce extraction because PEG can melt and form a wax before the alcohol can be completely evaporated or flashed off, an abuser may not be able to obtain a residue containing the active substance. These properties can allow for an oral drug delivery system that satisfies at least one of the categories in the FDA guidance (e.g., "physical and chemical barriers can change the physical form of an oral drug rendering it less amenable to abuse").

The PEG can be capable of allowing immediate release of the active substance, providing abuse deterrence, and/or ensuring the formation of a solid dosage form that is stable at elevated temperatures, for example 40° C. In some embodiments, the PEG provides all three. The dosage form of the present disclosure can accomplish the above capabilities by using a mixture of PEG molecules of at least two different average molecular weights. For example, the dosage form may include a first PEG having an average molecular weight between about 30,000 Daltons and 40,000 Daltons, and a second PEG having an average molecular weight about 3000 Daltons and 4000 Daltons.

In some embodiments, the first PEG has an average molecular weight of about 20,000, 21,000, 22,000, 23,000, 24,000, 25,000, 26,000, 27,000, 28,000, 29,000, 30,000, 30,500, 31,000, 31,500, 32,000, 32,500, 33,000, 33,500, 34,000, 34,500, 35,000, 35,500, 36,000, 36,500, 37,000, 37,500, 38,000, 38,500, 39,000, 39,500 or 40,000 Daltons. Any of these values may be used to define a range for the average molecular weight of the first PEG. For example, the first PEG can have an average molecular weight between about 31,000 Daltons and about 39,000 Daltons, between about 32,000 Daltons and about 38,000 Daltons, between about 33,000 Daltons and about 37,000 Daltons, between about 34,000 Daltons and about 36,000 Daltons, between about 30,000 Daltons and about 32,000 Daltons, between about 32,000 Daltons and about 34,000 Daltons, between about 36,000 Daltons and about 38,000 Daltons, or between about 38,000 Daltons and about 40,000 Daltons.

In some embodiments, the second PEG can have an average molecular weight of 3000, 3050, 3100, 3150, 3200, 3250, 3300, 3350, 3400, 3450, 3500, 3550, 3600, 3650, 3700, 3750, 3800, 3850, 3900, 3950 or 4000 Daltons. Any of these values may be used to define a range for the average molecular weight of the second PEG. For example, the second PEG can have an average molecular weight between about 3100 Daltons and about 3900 Daltons, between about 3200 Daltons and about 3800 Daltons, between about 3300 Daltons and about 3700 Daltons, between about 3400 Daltons and about 3600 Daltons, between about 3000 Daltons and 3200 Daltons, between about 3200 Daltons and about 3400 Daltons, between about 3600 Daltons and about 3800 Daltons, or between about 3800 Daltons and about 4000 Daltons.

In some embodiments, the ratio of the first PEG to the second PEG can be about 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19 or 1:20. Any of these values may be used to define a range for the ratio of the first PEG to the second PEG. For example, in some embodiments, the ratio of the first PEG to the second PEG can be between about 1:2 w/w and about 2:1 w/w, between about 1:3 w/w and about 1:1 w/w, between about 1:2 w/w and about 1:1 w/w, between about 1:1 w/w and about 2:1 w/w, between about 1:1 w/w and about 3:1 w/w, between about 1:4 w/w and about 1:10 w/w, between about 1:7 w/w and about 1:11 w/w, or between about 1:8 w/w and about 1:10 w/w. In other embodiments, the ratio of the first PEG to the second PEG can be less than about 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19 or 1:20. For example, a ratio of 1:10 is less than a ratio of 1:9.

The total wt % of PEG in the dosage form may vary depending on the active substance, stability, and release profile. In some embodiments, the first PEG and the second PEG together are at least about 5 wt %, 10 wt %, 15 wt %, 20 wt %, 25 wt %, 30 wt %, 35 wt %, 36 wt %, 37 wt %, 38 wt %, 39 wt %, 40 wt %, 41 wt %, 42 wt %, 43 wt %, 44 wt %. 45 wt %, 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 69.7 wt %, 70 wt %, 71 wt %, 72 wt %, 73 wt %, 74 wt %, 75 wt %, 76 wt %, 77 wt %, 78 wt %, 79 wt %, 80 wt %, 85 wt %, 88 wt %, 90 wt %, or 95 wt % of the dosage form.

In one embodiment, the formulation includes a disintegrant. A disintegrant promotes disintegration of the capsule, and dissolution of the active substance, after administration and upon contact with water. The disintegrant may be selected from sodium starch glycolate, cross-linked polyvinylpyrrolidone (e.g. crospovidone), cross-linked sodium carboxymethylcellulose (e.g. croscarmellose sodium) sodium bicarbonate/citric acid, alginic acid or combinations thereof. In particular embodiments, the disintegrant is selected from sodium starch glycolate, crospovidone and croscarmellose. The dosage form may contain about 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt % or 20 wt % of disintegrant. Any of these values may be used to define a range for the wt % of disintegrant. For example, the dosage form may contain between about 1.0 wt % and about 20 wt % of disintegrant. Particularly, the formulation may contain between about 1.0 wt % and about 10 wt % disintegrant or between about 5 wt % and about 8 wt % disintegrant. In certain embodiments, the dosage form includes 5 wt % sodium starch glycolate, 8 wt % sodium starch glycolate, 5 wt % crospovidone, or 5 wt % croscarmellose sodium. In another embodiment, the dosage form of the present disclosure excludes a disintegrant.

In some embodiments, the formulation includes a dye. A dye can be useful in deterring abuse by discouraging the abuser from intravenous injection. For example, extraction of the dye along with the active ingredient would result in a colored solution that would discourage the abuser from intravenous injection. Thus, in certain embodiments, the dye reduces abuse by extracting and injecting. The dye may be selected from known dyes suitable for use in pharmaceutical formulations or approved by the FDA for such use. For example, the dye may be FD&C Blue No. 2 or a 50/50 wt % solution of FD&C Blue No. 2 in PEG. In another embodiment, the dye may be a grey dye including FD&C Blue #1, FD&C Yellow #6, and FD&C Red #40. The dye may be in a 90% PEG 3350 blend. In certain embodiments, 14 mg of dye blend can be used in each capsule or about IA:mg of concentrated dye. In certain embodiments a grey dye is used since it is visually deterring and non-transparent. The dosage form may include about 0.10 wt %, 0.20 wt %, 0.30 wt %, 0.40 wt %, 0.50 wt %, 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, or 20 wt % dye. Any of these values may be used to define a range for the wt % of the dye. For example, the dosage form may contain between about 0.10 wt % and about 15 wt % dye. Particularly, the dosage form may contain between about 0.20 wt % and about 1.5 wt % dye, about 0.50 wt % and about 1.0 wt % dye, or about 7 to about 14 wt % dye. In certain embodiments, the dosage form may include about 1 mg, 1.4 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg or 30 mg of dye. In another embodiment, the dosage form of the present disclosure excludes a dye.

In some embodiments, the dosage form includes a first dye and a second dye, wherein the first dye has a high solubility in aqueous solution that is higher than the solubility of the second dye in aqueous solution. For example, in some embodiments the first dye has a solubility in aqueous solution of about 1 g, 5 g, 10 g, 30 g, 50 g, 100 g or 500 g in 1 L of aqueous solution and the second dye has a solubility in aqueous solution of about 1 mg, 5 mg, 10 mg, 30 mg, 50 mg, 100 mg, 500 mg, 1 g, or 10 g in 1 L of aqueous solution. In some embodiments, the second dye has a high solubility in non-aqueous solution that is greater than the solubility of the first dye in non-aqueous solution. For example, in some embodiments, the first dye has a solubility in non-aqueous solution of about 1 mg, 5 mg, 10 mg, 30 mg, 50 mg, 100 mg, 500 mg, 1 g, or 10 g in 1 L of non-aqueous solution, and the second dye has a solubility in non-aqueous solution of about 1 g, 5 g, 10 g, 30 g, 50 g, 100 g or 500 g in 1 L of non-aqueous solution. In some embodiments, the color of the first dye is substantially the same as the color of the second dye. In other embodiments, the color of the first dye is substantially different from the color of the second dye. For the purposes of the present disclosure, a dye is considered to be soluble in a solvent if about 1 g of the dye can be dissolved in about 10-30 mL of the solvent. For example, a dye is considered to be water soluble if about 1 g of the dye can be dissolved in 10-30 mL of water.

In another embodiment, the dosage form includes a preservative or antioxidant. The preservative or antioxidant can reduce or limit the degradation or deterioration of the abuse deterrent dosage form. For example, the components of the oral drug delivery system (e.g., active substances, PEG) may undergo degradation (e.g., oxidative reduction, chain cleavage) due to oxidation. Preventing degradation can help maintain the abuse deterrent properties of the formulation. For instance, the molecular weight of PEG in the formulation affects the resistance to grinding, for example, with a coffee grinder. The addition of a preservative or antioxidant in the formulation that reduces or eliminates the degradation of the molecular weight of PEG may be useful in maintaining the abuse deterrence properties of the dosage form. In addition to maintaining abuse deterrence, the addition of a preservative or antioxidant in the dosage form may be necessary to prevent premature degradation of the active substance over the shelf life of the dosage form.

The preservative or antioxidant may be selected from preservatives or antioxidants known to one skilled in the art for use in pharmaceutical formulations, such as citric acid, ascorbic acid, ascorbyl palmitate, butylated hydroxyanisole (BHA), butylated hydroxytoluene (BHT), erythorbic acid, hypophosphorous acid, lactobionic acid, monothioglycerol, potassium metabisulfite, propyl gallate, racemethionine, sodium bisulfite, sodium formaldehyde sulfoxylate, sodium metabisulfite, sodium sulfite, sodium thiosulfate, stannous chloride, sulfur dioxide and tocopherols. The formulation, or dosage form, may contain between about 0.1 wt % and about 2.0 wt %, or about 0.25 wt % and about 0.75 wt % of preservative or antioxidant. In another embodiment, the dosage form of the present disclosure excludes a preservative or antioxidant.

In some embodiments, the dosage form includes one or more excipients that form a gel in the presence of an alcohol. The alcohol gelling/thickening agent reduces or limits the potential for abuse by preventing extraction of the active substance from the dosage form. For example, when introduced to an alcohol solution, the components of the dosage form (e.g., active substances, PEG) may become trapped in a gel/viscous liquid which prevents extraction and subsequent alcohol evaporation to produce a pure active substance. In one embodiment, the alcohol gelling/thickening agent does not form a gel in the presence of water. The dosage form can contain up to about 1%, 2%, 3%, 4%, 5%, 6%. 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or about 40%. These values can be used to define a range, such as about 0.1 wt % to about 40 wt % alcoholic gelling/thickening agent. In another embodiment, the dosage form of the present disclosure does not contain an alcohol gelling/thickening agent.

The alcohol gelling/thickening agent may be a gelling or thickening agent known to one skilled in the art for use in pharmaceutical formulations, such as acacia, alginic acid, bentonite, calcium acetate, carbomers, carboxymethylcellulose, ethylcellulose, gelatin, hydroxyethylcellulose, hydroxypropyl cellulose, magnesium aluminum silicate, methylcellulose, poloxamers, polyvinyl alcohol, polyvinyl acetate, polyvinylpyrrolidone, sodium alginate, sorbitol derivatives, tragacanth, or xanthan gum.

The dosage form may additionally include at least one additive independently selected from surfactants, bulking agents, lubricants, flavorings or combination thereof.

The abuse deterrent dosage form of the present disclosure is capable of immediate release of the active substance. The dosage form may be manufactured to provide a composition exhibiting an immediate release profile of at least one active substance. As used herein, "immediate release" refers to a dosage form that releases the active substance or a pharmaceutically acceptable salt thereof, e.g., oxycodone HCl or hydrocodone bitartrate, substantially completely into the gastrointestinal tract of the user within a period of less than an hour, and often less than about 45 minutes or 30 minutes from ingestion. In one embodiment, the amount of active substance released from the dosage form, e.g., oxycodone HCl or hydrocodone bitartrate, by exposure to deaerated water within 45 minutes is greater than or equal to 75%. In another embodiment, the amount of active substance released from the dosage form, e.g., hydrocodone bitartrate, by exposure to a 0.1 N hydrochloric acid solution within 30 minutes is greater than or equal to 90%. In other embodiment, the amount of active substance released from the dosage form, e.g., oxycodone HCl, within 45 minutes is greater than or equal to 75%.

In one embodiment, the dosage form of the present disclosure releases greater than or equal to about 75% of the active substance within 45 minutes after administration or via dissolution testing. Particularly, the dosage form releases greater than or equal to about 80%, about 85%, about 90%, or about 95% of the active substance within 45 minutes after administration or via dissolution testing.

In other embodiments, the dosage form of the present disclosure releases greater than or equal to about 90% of the active substance within 30 minutes after administration or via dissolution testing. Particularly, the dosage form releases greater than or equal to about 92%, about 94%, about 96%, or about 98% of the active substance within 30 minutes after administration or via dissolution testing.

The present disclosure also relates to an oral, immediate release, abuse deterrent dosage form including an active substance susceptible to abuse and PEG with a weighted average molecular weight between about 6200 Daltons and about 7800 Daltons. In one embodiment, dosage forms containing an average molecular weight of PEG in this particular range have several desirable characteristics including immediate release of the active substance, stability at high temperature conditions (e.g., 40° C. with 75% relative humidity), relatively low viscosity at elevated temperatures (e.g., a viscosity less than or equal to 2000 cP at 75° C.), and/or a relatively high particle size after grinding (e.g., greater than or equal to 50% of the particles having a diameter greater than or equal to 500 μm after grinding, such as for 30 seconds at 10,000 RPM). Dosage forms including PEG with an average molecular weight between about 6200 Daltons and about 7800 Daltons may be prepared by combining two or more PEGs with different molecular weights. For example, any of the PEGs described herein (e.g., PEG 3350 and PEG 35000) may be combined to prepare a dosage form including PEG with an average molecular weight range between about 6200 Daltons and about 7800 Daltons.

In particular embodiments, the dosage form includes PEG, or two or more PEGs, with an average molecular weight of about 5000, 5015, 5100, 5200, 5300, 5400, 5500, 5600, 5700, 5800, 5900, 6000, 6100, 6200, 6300, 6400, 6500, 6515, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10,000, 10,100, 10,200, 10,300, 10,400, 10,500, 10,600, 10,700, 10,800, 10,900, 11,000, 11,100, 11,200, 11,300, 11,400, 11,500, 11,600, 11,675, or 11,700 Daltons. Any of these values may be used to define a range of average molecular weights for PEG, or PEGs, depending on the application. For example, in some embodiments, the dosage form includes PEG, or PEGs, with an average molecular weight between about 6200 Daltons and about 6515 Daltons, between about 6515 Daltons and about 6800 Daltons, or between about 6200 Daltons and about 6800 Daltons.

In other embodiments, the present disclosure relates to an oral, immediate release, abuse deterrent dosage form including an active substance susceptible to abuse, a first PEG having a melting point greater than or equal to about 60° C. and a second PEG having a melting point less than or equal to about 57° C. The dosage form can be a solid at 40° C./75% relative humidity, and at least 90% of the active ingredient can be released from the dosage form within 30 minutes following administration or via dissolution testing. The dosage form can be a solid at 40° C./75% relative humidity, and at least 75% of the active ingredient can be released from the dosage form within 45 minutes following administration or via dissolution testing.

The melting point of PEG can be positively correlated with molecular weight, i.e. higher molecular weight PEGs have higher melting points. For example, PEGs with an average molecular weight up to 400 Daltons can be considered nonvolatile liquids at room temperature. PEG 600, for example, has a melting range of about 17 to 22° C., and may be liquid at room temperature but waxy at lower temperatures. PEGs with an average molecular weight of 800 to 2000 Daltons can be considered waxy materials at room temperature with a relatively low melting range. For example, PEG 1500 has a melting point of about 42-46° C. PEGs with an average molecular weight above 3000 can be considered solids. For example, PEG 3350 has a melting point of about 53-57° C., and PEG 35,000 has a melting point of about 60-65° C. By combining a PEG with a relatively low melting point (e.g., PEG 3350) with a PEG with a relatively high melting point (e.g., PEG 35,000) a dosage form with several desirable properties can be formed, including immediate release of an active substance, stability at high temperatures (e.g., 40° C. with 75% relative humidity), relatively low viscosity at elevated temperatures (e.g., less than or equal to 2000 cP at 75° C.), and/or a relatively high particle size after grinding (e.g., greater than or equal to 50% of the particles having a diameter greater than or equal to 500 μm) and/or the incorporation of a chemical barrier which makes it difficult to separate the active substance from the rest of the formulation.

In some embodiments, the dosage form includes a first PEG having a melting temperature greater than or equal to about 52° C., 53° C., 54° C., 55° C., 56° C., 57° C., 58° C., 59° C., 60° C., 61° C., 62° C., 63° C., 64° C., 65° C., 66° C., 67° C., 68° C. 69° C., or 70° C. Any of these values may be used to define a range of melting temperatures for the first PEG depending on the application. For example, the dosage form may include a first PEG having a melting temperature from about 52° C. to about 60° C., from about 55° C. to about 60° C., from about 53° C. to about 57° C., from about 53° C. to about 56° C., from about 55° C. to about 58° C., from about 60° C. to about 65° C., or from about 60° C. to about 70° C.

In some embodiments, the dosage form includes a second PEG having a melting temperature less than or equal to about 5° C., 10° C., 15° C., 16° C., 17° C., 18° C., 19° C., 20° C., 21° C., 22° C., 23° C., 24° C., 25° C., 25° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 55° C., 56° C., or about 57° C. Any of these values may be used to define a range of melting temperatures for the second PEG depending on the application. For example, the dosage form may include a second PEG having a melting temperature between about 17° C. and about 22° C. between about 42° C. and about 46° C., between about 53° C. and about 57° C., or between about 42° C. and about 57° C.

In some embodiments, the dosage form includes a first PEG and a second PEG, wherein the first PEG and the second PEG combined have a melting temperature of about 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C. Any of these values may be used to define a range of melting temperatures for the combined first and second PEG depending on the application. For example, the first PEG and the second PEG combined may have a melting temperature between about 53° C. and about 65° C.

In other embodiments, the present disclosure relates to an oral, immediate release, abuse deterrent dosage form including an active substance susceptible to abuse, a first PEG having a melting point greater than or equal to about 60° C. and a second PEG having a viscosity at 100° C. less than or equal to about 110 cSt. The dosage form can be a solid at 40° C./75% relative humidity, and at least 75% of the active ingredient can be released from the dosage form within 45 minutes following administration or via dissolution testing or at least 90% of the active ingredient can be released from the dosage form within 30 minutes following administration or via dissolution testing.

In some embodiments, the dosage form includes a second PEG having a viscosity at 100° C. of less than or equal to about 500 cSt, 450 cSt, 400 cSt, 350 cSt, 300 cSt, 250 cSt, 200 cSt, 190 cSt, 180 cSt, 170 cSt, 160 cSt, 158 cSt, 150 cSt, 140 cSt, 130 cSt, 123 cSt, 120 cSt, 110 cSt, 105 cSt, 100 cSt, 99 cSt, 93 cSt, 90 cSt, 87 cSt, 80 cSt, 76 cSt, 75 cSt, 73 cSt, 70 cSt, 67 cSt, 60 cSt, 50 cSt, 49 cSt, 48 cSt, 47 cSt, 46 cSt, 45 cSt, 44 cSt, 43 cSt, 42 cSt, 41 cSt, 40 cSt, 39 cSt, 38 cSt, 37 cSt 36 cSt, 35 cSt, 34 cSt, 33 cSt, 32 cSt, 31 cSt, 30 cSt, 29 cSt, 28 cSt, 27 cSt, 26 cSt, 25 cSt, 24 cSt, 23 cSt, 22 cSt, 21 cSt, 20 cSt, 19 cSt, 18 cSt, 17 cSt, 16 cSt, 15 cSt, 14 cSt, 13 cSt, 12 cSt, 1 J cSt, 10 cSt, 9 cSt, 8 cSt, 7 cSt, 6 cSt, 5 cSt, or about 4 cSt. Any of these values may be used to define a range of viscosities for the second PEG depending on the application. For example, the dosage form may include a second PEG having a viscosity between about 4.0 cSt and about 49.0 cSt, between about 16.0 cSt and about 49.0 cSt, between about 25.0 cSt and about 32.0 cSt, or between about 76 cSt and about 110 cSt.

In some embodiments, the formulation of the present disclosure can have a viscosity at 100° C. of about 40 cSt, 41 cSt, 42 cSt, 43 cSt, 44 cSt, 45 cSt, 46 cSt, 47 cSt, 48 cSt, 49 cSt, 50 cSt, 51 cSt, 52 cSt, 53 cSt, 54 cSt, 55 cSt, 56 cSt, 57 cSt, 58 cSt, 59 cSt, 60 cSt, 61 cSt, 62 cSt, 63 cSt, 64 cSt, 65 cSt, 66 cSt, 67 cSt, 68 cSt, 69 cSt, 70 cSt, 71 cSt, 72 cSt, 73 cSt, 74 cSt, 75 cSt, 76 cSt, 77 cSt, 78 cSt, 80 cSt, 90 cSt, 100 cSt, 110 cSt, 120 cSt, 130 cSt, 140 cSt, 150 cSt, 158 cSt, 160 cSt, 170 cSt, 180 cSt, 190 cSt, 200 cSt, 250 cSt, 300 cSt, 350 cSt, 400 cSt, 450 cSt 500 cSt, 600 cSt, 700 cSt, 800 cSt, 900 cSt, 1000 cSt, 1100 cSt, 1200 cSt, 1300 cSt, 1400 cSt, 1500 cSt, 1600 cSt, 1700 cSt, 1800 cSt, 1900 cSt, or about 2000 cSt. Any of these values may be used to define a range of viscosities for the formulation of the present disclosure depending on the application. For example, the formulation of the present disclosure may have a viscosity between about 500 cSt and about 2000 cSt, or between about 800 cSt and about 1900 cSt. In some embodiments, the formulation or dosage form is a solid at room temperature and/or at 100° C. and has not measureable viscosity.

In another embodiment, the present disclosure relates to a process for the production of an oral, immediate release, abuse deterrent dosage form including preparing a homogenized suspension of at least one active substance susceptible to abuse, a first PEG, and a second PEG. For example, the first PEG can have an average molecular weight between about 30,000 Daltons and about 40,000 Daltons, and the second PEG can have an average molecular weight between about 3000 Daltons and about 4000 Daltons. The ratio of the first PEG to the second PEG can be less than about 1:4 w/w. The process can further include dispensing or filling a homogenized suspension into a capsule to produce the dosage form. In some embodiments, the capsule can be formed by joining a capsule body with a capsule cap. The first PEG and the second PEG together may be any wt % of the dosage form as described herein, for example at least about 60 wt % of the dosage form. In some embodiments of the processes described herein, the active substance is hydrocodone bitartrate. In other embodiments, the active substance is oxycodone HCl. In certain embodiments, the abuse deterrent dosage forms of the present disclosure are capsules.

The abuse deterrent dosage forms of the present disclosure may be produced by liquid filled encapsulation. Liquid filled encapsulation is a process in which active pharmaceutical ingredients are suspended or emulsified in a carrier matrix and filled into capsules. The capsules are usually made of hard gelatin or hydroxypropyl methylcellulose. One of the advantages of this dosage form is that it requires fewer excipients and processing steps than other traditional compressed solid dosage forms. The internal solid phase API (e.g., oxycodone HCl or hydrocodone bitartrate) can be suspended in a PEG external fluid phase. In one embodiment, PEGs with average molecular weights greater than about 1500 Daltons are ideal for liquid filled capsules because they are thermoplastics that melt at temperatures below the melting point of the hard gelatin capsule (<70° C.) and are solids at room temperature. If the filling material is liquid at room temperature, a banding process can be used. This process adds a gelatin band around the point where the capsule body and cap join to create a unified capsule body to prevent leakage. In some embodiments, the formulation of the present disclosure can include a band.

In one embodiment, the liquid fill process can begin by dispensing excipients (e.g., PEG and stabilizers/preservatives) and API according to theoretical percent weights of the final capsule fill weight. Following this step, the PEG powders or flakes and dyes are pre-melted before they are added to a homogenizing mixing kettle which can maintain the PEG above its melting point via jacketing on the kettle. When the PEG is completely fluid, the API and other non-melting stabilizers and/or preservatives can be mixed in to form a homogenized suspension. This can occur with the aid of mechanical agitation by way of several internal stirring arms. Once a homogenized suspension is attained (in some embodiments newer kettles can be equipped with NIR probes to indicate when this happens), the suspension can be pumped through jacketed hoses (to maintain the internal kettle temperature to prevent solidification in the hose) to a hopper on the capsule filling machine. An illustration of a capsule filling machine is provided in FIG. 1.

The capsule filling hopper can also be jacketed to heat the suspension to prevent solidification. The capsule filling machine can contain a separate hopper which operators fill with hard gelatin capsules. The hopper can feed into a rectifying drum which can align all capsules in the same direction. Once aligned, the capsules can sit vertically in a cap disk which can allow for separation of the body and cap via vacuum. To fill the capsule, a positive displacement piston pump can be used to draw the product in from the jacketed hopper and dispense the suspension into the capsule body through a set of changeable nozzles. Fill weight adjustment can be achieved by varying the piston stroke of the pump. These changes can be made throughout the process due to frequent in-process capsule weight checks.

Once the capsule body is filled, the capsule body and cap can be joined via pusher pins which raise the capsule body upwards and into the capsule cap, which are held in place above the capsule body by a joining block. The pusher pins can then push the unified capsule out of the cap disk and discharge them from the machine. The capsules can then be allowed to cool at room temperature on trays and can be each weight checked via a capsule weigh checking machine. Following this, the capsules can then be placed into a final output drum. Automatic capsule filling machines can have the ability to produce 500 to 150,000 capsules an hour with a very high degree of accuracy.

In some embodiments, the present disclosure relates to a dosage form as described herein prepared by filling a capsule body with a heated homogenized suspension including an active substance, a first PEG and a second PEG. In some embodiments, the homogenized suspension including an active substance, a first PEG, and a second PEG melts at a temperature of about 42° C., 43° C., 44° C., 45° C. 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C. 73° C., 74° C., or 75° C. Any of these values may be used to define a range of melting temperatures for the homogenized suspension. For example, in certain embodiments, the homogenized suspension has a melting temperature between about 53° C. and about 65° C. In particular embodiments, the homogenized suspension including an active substance, a first PEG and a second PEG melts at temperatures below 77° C., i.e., the melting point of the hard gelatin capsule. In another embodiment, the present disclosure relates to a method of treating pain including administering to an individual in need thereof a therapeutically effective amount of a dosage form as described herein. The dosage form can be used for the management of moderate to severe pain where the use of an opioid analgesic is appropriate. The dosage form can provide rapid onset of analgesia for the treatment of moderate to severe pain. The dosage form. e.g., a hard gelatin capsule, can be administered orally every 4-6 hours as needed.

The disclosures of all cited references including publications, patents, and patent applications are expressly incorporated herein by reference in their entirety. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

Initial testing and evaluation experiments for the immediate release ADF liquid filled capsule were based on suspending an API in PEG and filling it to weight into a hard gelatin capsule which then solidifies into a wax at room temperature. Some of these experiments used acetaminophen (APAP) as a tracer drug in place of C-II narcotics. Oxycodone HCl and APAP are both soluble in reaerated water. The USP monograph for pooled hydrocodone bitartrate and acetaminophen tablets specifies 80% (Q) +10% release of both drugs in 30 minutes in 0.1N HCl, indicating both are capable of immediate release. As a result, APAP was expected to be a viable alternative for experimentation.

A formulation was prepared containing 30 mg APAP and a 50:50 ratio of PEG 3350:1500 g/mol and 0.50% FD&C dye in size 3 white opaque capsules. Three capsule fill weights were evaluated: 100 mg, 150 mg, and 200 mg. These formulations were tested for dissolution. The USP criteria for immediate release of oxycodone HCl is 500 mL purified water as media, Q=70% at 45 minutes, Specification=75% (Q+5%), apparatus 2 (paddles), 50 rpm. All capsule weights proved to release immediately, with the 150 mg and 200 mg formulations releasing completely at 20 minutes. 100 mg capsule fill would be preferred to decrease material costs. Table 1 below list the dissociation data of size 3 capsules containing 30 mg APAP, a 50:50 ratio of PEG 3350:1500 g/mol, and 0.5% FD&C dye.

TABLE 1

| Batch | Capsule fill | 20 Minutes | Average | 45 Minutes | Average |
|---|---|---|---|---|---|
| 18-1 | 100 mg | 78.18 | 78.07 | 86.25 | 86.19 |
| 18-2 | | 78.66 | | 88.23 | |
| 18-3 | | 77.37 | | 84.11 | |
| 19-1 | 150 mg | 92.76 | 95.48 | 96.95 | 95.17 |
| 19-2 | | 98.55 | | 100.69 | |
| 19-3 | | 95.13 | | 87.86 | |
| 20-1 | 200 mg | 92.74 | 91.82 | 96.68 | 96.59 |
| 20-2 | | 88.16 | | 96.59 | |
| 20-3 | | 94.57 | | 96.50 | |

These dosage forms contain water-and ethanol-soluble FD&C dyes, e.g., 0.5% FD&C dye, to deter extraction of the API and intravenous injection of the solution. Further rendering of the drug solution would be required to separate the pure API from the PEG and FD&C dyes.

PEG 1450 (NF grade available from Dow Chemical Company) can be used in place of PEG 1500 in the oxycodone HCl dosage forms. Additional exemplary oxycodone HCl dosage forms are shown in Table 2 below. 1% citric acid may be used in the dosage forms as an API stabilizer.

TABLE 2

| Dosage | Oxycodone HCl (mg) | PEG 3350 (mg) | PEG 1450 (mg) | FD&C Dye (mg) | Citric Acid (mg) | Total Capsule Fill (mg or %) |
|---|---|---|---|---|---|---|
| 5 | 5 | 44.25 | 44.25 | 0.5 | 1 | 100 |
| 15 | 15 | 34.25 | 34.25 | 0.5 | 1 | 100 |
| 30 | 30 | 19.25 | 19.25 | 0.5 | 1 | 100 |

| Dosage | Oxycodone HCl (%) | PEG 3350 (%) | PEG 1450 (%) | FD&C Dye (%) | Citric Acid (%) | Total Capsule Fill (mg or %) |
|---|---|---|---|---|---|---|
| 5 | 5 | 41-47 | 41-47 | 0.25-0.75 | 0.5-2 | 100 |
| 15 | 15 | 31-37 | 31-37 | 0.25-0.75 | 0.5-2 | 100 |
| 30 | 30 | 16-22 | 16-22 | 0.25-0.75 | 0.5-2 | 100 |

Example 2

Immediate Release ADF Liquid Fill Capsules including PEG 35000

The dissolution rate, ADF properties and melt temperatures of additional immediate release ADF oxycodone HCl liquid fill capsule formulations containing varying amounts of PEG 1450 and PEG 35000 were evaluated. Acetaminophen (APAP) was used as a tracer drug for oxycodone HCl. The formulations are shown in Table 3 below. The target amount of APAP was 30 mg per capsule, and the target fill weight was 100 mg (batch number 92) or 200 mg (batch numbers 93-94). The capsules contained 30% w/w (batch number 92) or 15% w/w (batch numbers 93-94) APAP. Size 3 opaque hard gelatin capsules were used.

Dissolution was tested using the following criteria: Q= not less than 70% dissolved at 45 minutes, and the specification =Q+5% (75%) dissolved at 45 minutes. As shown in Table 3, the average dissolution for the three formulations ranged from 87% to 98%. Accordingly, all of the formulations met the specification of at least 75% dissolution at 45 minutes.

As mentioned above, it is generally accepted that any particle greater than 500 μm in diameter cannot be sufficiently absorbed by the blood vessels in the nasal mucosa. Thus, in one embodiment, a formulation is considered to deter intranasal abuse if ≥75% of the particles are ≥500 μm in diameter after grinding. As shown in Table 3, the percentage of particles ≥500 μm in diameter after grinding ranged from 90% to 92%. Thus all of the oxycodone formulations met the standard of ≥75% of the particles being ≥500 μm in diameter after grinding.

TABLE 3

Dissolution and Particle Size after Grinding for Oxycodone HCl Formulations Including PEG 35000 and PEG 1450.

| | Excipients | | | Grinding/ | | |
|---|---|---|---|---|---|---|
| | % | % of | Dissolution | | Particle Size | |
| Batch Number | % PEG 35000 | PEG 1450 | Overall Fill | % @ 45 min** | Average | % ≥500 μm | % <500 μm |
| 92-1 | 100 | 0 | 70 | 100 | 87 | 97 | 8 |
| 92-2 | | | | 83 | | | |
| 92-3 | | | | 77 | | | |
| 93-1 | 82 | 18 | 85 | 91 | 90 | 91 | 9 |
| 93-2 | | | | 90 | | | |
| 93-3 | | | | 88 | | | |
| 94-1 | 59 | 41 | | 98 | 98 | 90 | 10 |
| 94-2 | | | | 99 | | | |
| 94-3 | | | | 95 | | | |

The oxycodone HCl formulations were also analyzed to determine melting temperature. The capsules were held at 40° C./75% relative humidity for 72 hours. As shown in Table 4 below, the batch number 92 and 93 formulations containing 100% and 82% PEG 35000, respectively, were solid at these conditions, while the batch number 94 formulation containing 59% PEG 35000 had a much softer fill.

TABLE 4

Melt study of Oxycodone HCl formulations.

| Batch Number | % PEG 1450 | % PEG 35000 | % of Overall Fill | Designation* | Notes |
|---|---|---|---|---|---|
| 92 | 0 | 100 | 70 | 1 | No evidence of melt |
| 93 | 18 | 82 | 85 | 1 | No evidence of melt |
| 94 | 41 | 59 | | 2 | Much softer fill |

*1 (one) = Solid, 5 (five) = Thick Liquid

The dissolution, particle size after grinding, and color extraction of two additional formulations of oxycodone HCl (batch numbers 11 and 12) containing varying percentages of PEG 35000 and PEG 1450 were determined as described above. The formulations also contained 1% citric acid and 14% Grey Dye. Both formulations used a size 3 opaque hard gelatin capsule with a target fill weight of 100 mg. APAP was used as a tracer drug for oxycodone HCl. The target amount of APAP was 5 mg (5% w/w) for batch number 11 and 30 mg (30% w/w) for batch number 12. For dissolution, Q=Not less than 70% dissolved at 45 minutes, and the specification =Q+5% (75%) dissolved at 45 minutes. As a reference, an acceptable particle size after grinding is ≥75% particles ≥500 μm in diameter. As a reference, an acceptable color scale designation after extraction of the dye is ≥4 on a scale of 1 to 5, with 5 being the highest level of color.

As shown in Table 5 below, both oxycodone HCl formulations met the criteria for dissolution rate, particle size after grinding, and color extraction.

TABLE 5

Dissolution, Particle Size after Grinding, and Color Extraction of Oxycodone HCl Formulations containing PEG 35000 and PEG 1450.
Oxycodone HCl Formulation

| | Excipients | | | | | Grinding/ | Particle Size | | Extraction |
|---|---|---|---|---|---|---|---|---|---|
| Batch Number | % PEG 35000 | % PEG 1450 | % Citric Acid | % Grey Dye | % of Overall Fill | Dissolution Avg. % @ 45 min | % ≥500 μm | % <500 μm | Color Scale Designation |
| 11-1 | 48 | 32 | 1 | 14 | 95 | 106 | 90 | 10 | 5 |
| 11-2 | | | | | | | | | |
| 11-3 | | | | | | | | | |
| 12-1 | 33 | 22 | | | 70 | 96 | 89 | 11 | 5 |
| 12-2 | | | | | | | | | |
| 12-3 | | | | | | | | | |

In one embodiment, hot melt fill capsules are sufficiently viscous at elevated temperatures to allow for flow of the fill into the capsules. Accordingly, additional oxycodone HCl formulations containing PEG 35000 and either PEG 3350 or PEG 1450 were evaluated by measuring viscosity at 75° C. at 50 rpm. Formulations were weighed out according to total wt % of a 15 g batch. Each formulation was poured into a viscosity testing crucible and placed in an 80° C. water bath to melt. Once fully melted, the formulations were mixed using a stainless steel spatula and transferred to a Brookfield DV-II+ Pro Viscometer (VIS29 NCD: Upon Use) utilizing Spindle: S27 (Small Sample Adapter). The viscometer was equipped with a water jacketed crucible platform. Once the melt temperature reached 75° C., a viscosity reading was taken in centipoise (cP). Based on manufacturer specifications, an acceptable viscosity for the purposes of this study is ≤1000 cP. The particle size after grinding and stability at 40° C./75% relative humidity (RH) was also determined. For the grinding analysis, an acceptable particle size after grinding was considered to be ≥75% particles ≥500 μm in diameter. All formulations were size 3 opaque hard gelatin capsules.

As shown in Table 6 below, batch number 100 containing 11% PEG 35000 and 44% PEG 1450 had a viscosity of 1288 cP at 75° C./50 rpm, above the manufacturer specification of ≤1000 cP. Accordingly, viscosity was not measured for the formulations containing higher percentages of PEG 35000 (i.e. batch numbers 97-99). In addition, batch number 100 was not sufficiently stable for storage, since this formulation was a very viscous liquid at the stability test conditions of 40° C./75% RH.

Although batch number 101 containing 5.5% PEG 35000 and 49.5% PEG 1450 had an acceptable viscosity (705 cP) at 75° C./50 rpm, the stability tests revealed that this formulation was a very viscous liquid at 40° C./75% RH, and thus was not stable for storage. Because the formulations containing 11% PEG 35000 (batch number 100) and 5.5% PEG 35000 (batch number 101) were not sufficiently stable for storage, stability of batch number 103 containing 7.7% PEG 35000 was not determined.

Formulations containing PEG 35000 and PEG 3350 were also evaluated. As shown in Table 6 below, the formulation containing 6.97% PEG 35000 and 62.7% PEG 3350 (batch number 104) and the formulation containing 7.7% PEG 35000 and 69.3% PEG 3350 (batch number 105) met all of the criteria for particle size after grinding, viscosity, and stability.

TABLE 6

Particle size, Viscosity, and Stability for Oxycodone HCl Formulations Containing PEG 35000.

| Batch | % PEG 35000 | % PEG 3350 | % PEG 1450 | Peg Ratio | Grey Dye | % API | Capsule Target Weight (mg) | Particle Size % ≥500 μm*** | Particle Size % <500 μm | Viscosity (cP) | Stability at 40° C./75% RH |
|---|---|---|---|---|---|---|---|---|---|---|---|
| 97 | 27.5 | 0 | 27.4 | 50:50 | 14 | 30 | 100 | 83.0 | 17.0 | NA | Softened Wax, non-liquid |
| 98 | 22 | | 33 | 40:60 | | | | 91.4 | 8.6 | NA | Softened Wax, non-liquid |
| 99 | 16.5 | | 38.5 | 30:70 | | | | 90.1 | 9.9 | NA | Semi-solid |
| 100 | 11 | | 44 | 20:80 | | | | 95.7 | 4.3 | 1288 | Very viscous liquid |
| 101 | 5.5 | | 49.5 | 10:90 | | | | 99.6 | 0.4 | 705 | Very viscous liquid |
| 103 | 7.7 | | 69.3 | 10:90 | 7 | 15 | 200 | NA | NA | 298 | NA |
| 102 | 5.5 | 49.5 | 0 | 10:90 | 14 | 30 | 100 | 78.8 | 21.2 | 1045 | Softened Wax, non-liquid |
| 104 | 6.97 | 62.7 | | 10:90 | 9.33 | 20 | 150 | 79.9 | 20.1 | 745 | Softened Wax, non-liquid |
| 105 | 7.7 | 69.3 | | 10:90 | 7 | 15 | 200 | 77.5 | 22.5 | 620 | Softened Wax, non-liquid |
| 106 | 15.4 | 61.6 | | 20:80 | 7 | 15 | 200 | 85.1 | 14.9 | 1375 | NA |

Example 3

Evaluation of Dyes

Figure 2A:
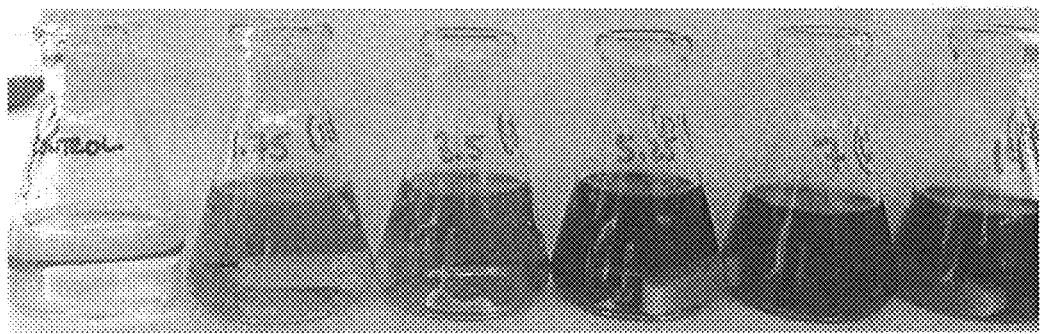
FIG. 2A shows solutions of grey dye before filtering.
Figure 2B:
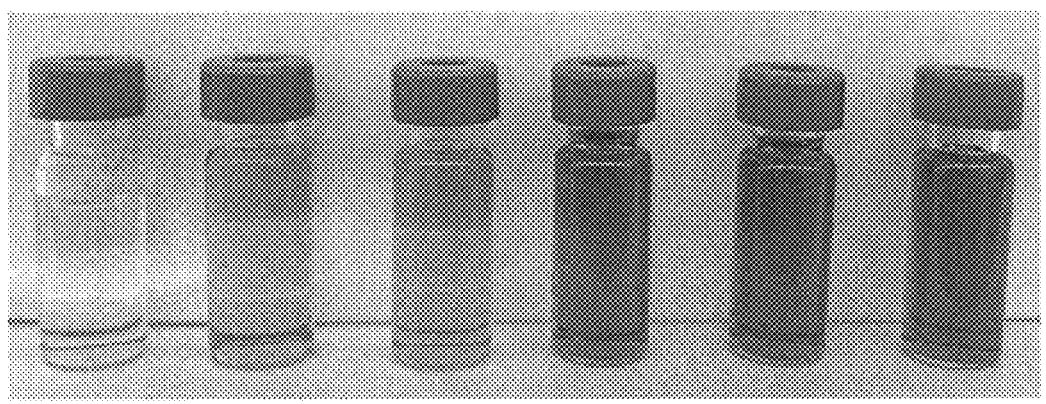
FIG. 2B shows solutions of grey dye after filtering.

Numerous dyes were evaluated for their potential to deter intravenous abuse. Varying concentrations of FD&C Blue #2, green (FD&C Blue #2 and FD&C Yellow #5), FD&C Yellow #5, FD&C Red #40, and grey dye (FD&C Blue#1, FD&C Yellow #6, FD)&C Red #40) were evaluated by dissolving them in a 95% ethanol 5% purified water (190 proof) solution and passing the solution through a syringe filter. After syringe filtering the dye solutions were visually evaluated for color intensity and rated on a scale of 0 to 5, with 0 indicating no color and 5 indicating dark, significant color. As shown in the Table 7 below, the blue and green dyes exhibited the highest color intensity at low concentrations, e.g. 0.25% w/w. Solutions of grey dye before and after filtering are shown in FIGS. 2A and 2B, respectively. The grey dye was particularly striking and less appealing. An acceptable color scale designation after extraction of the dye is ≥4 on a scale of 1 to 5, with 5 being the highest level of color.

TABLE 7

Evaluation of Various Dyes at Varying Concentrations in 190 Proof Alcohol

| Batch | Dye Color | Dye (% w/w) | Dye (mg) | Color Number* |
|---|---|---|---|---|
| 66 | Blue | 0.25 | 1.75 | 4 |
| 67 | Blue | 0.50 | 3.50 | 5 |
| 68 | Blue | 0.75 | 5.25 | 5 |
| 69 | Blue | 1.00 | 7.00 | 5 |
| 70 | Green | 0.25 | 1.75 | 4 |
| 71 | Green | 0.50 | 3.50 | 4 |
| 72 | Green | 0.75 | 5.25 | 4 |
| 73 | Green | 1.00 | 7.00 | 4 |
| 74 | Yellow | 0.25 | 1.75 | 3 |
| 75 | Yellow | 0.50 | 3.50 | 4 |
| 76 | Yellow | 0.75 | 5.25 | 5 |
| 77 | Yellow | 1.00 | 7.00 | 5 |
| 78 | Red | 0.11 | 0.75 | 2 |
| 79 | Red | 0.21 | 1.50 | 3 |
| 80 | Red | 0.43 | 3.00 | 4 |
| 81 | Red | 0.63 | 4.44 | 5 |
| 82 | Grey | 0.25 | 1.75 | 2 |
| 83 | Grey | 0.50 | 3.50 | 2 |
| 84 | Grey | 0.75 | 5.25 | 4 |
| 85 | Grey | 1.00 | 7.00 | 4 |
| 86 | Grey | 2.00 | 14.00 | 5 |

In one embodiment, the dye can be grey. Grey can be chosen because it is darker than the others and can be effective at a lower relative concentration. Grey dye can allow for the most visually deterring form with the least amount of dye present in the formulation.

Example 4

Immediate Release ADF Oxycodone HCl Liquid Fill Capsules

Abusers of opioid products often adulterate the product to promote more rapid release of the active ingredient. The products can be chewed and swallowed, crushed and inhaled, or extracted in water or alcohol (either crushed or intact) to produce a solution that can be used for intravenous administration or dried for insufflation of a purified product. Adulteration of the products can enable a more rapid delivery of active than can be achieved by ingestion of the intact product. This rapid onset, high exposure is associated with euphoria, drug liking, and greater abuse potential.

Current abuse-deterrent formulations have limitations. Insufflation is a common route of abuse for oxycodone HCl products. To be attractive for insufflation, crushing a product should yield particles of less than 500 μm to allow uptake of the active substance though the nasal mucosa. Therefore, abuse deterrent formulations can be made to discourage crushing or breaking of tablets to yield particles less than 500 μm. Test methods using flat platens to crush the product as a criterion for abuse deterrence is not meaningful. All C-II narcotic drug products tested can be cut with an edged surface (e.g., scissors or a razor blade) and therefore can potentially be abused, with forces that are substantially lower than what has been reported using the breaking strength test or equivalent (e.g., >500 N). Flattening the tablets using forces greater than 500 N (with traditional "tablet breaking force" definitions) does not address abuse deterrence potential in the tested C-II narcotic drug products.

Grinding can be a better evaluation of the relative resistance of marketed products to abuse. The formulation of the present disclosure compares favorably against Roxicodone® with respect to a decrease in the percentage of particles produced after grinding that are smaller than 500 μm. Statistically different results emerge between the formulation of the present disclosure and Roxicodone® in the degree of resistance to grinding, with the formulation of the present disclosure yielding less than 50% of particles smaller than 500 μm, compared with approximately 77% of particles less than 500 μm for Roxicodone®. Better resistance to grinding can be due to differences in the manufacturing processes and/or the excipients employed for the two products.

The formulation of the present disclosure can be resistant to abuse by nasal insufflation or extraction due to, in part, the waxy nature of the formulation contents and the solubility of the excipients. The excipients can be both water and alcohol soluble to create a formulation that makes it time consuming and costly to extract oxycodone HCl from the formulation contents without also extracting the excipients. A high molecular weight PEG can be included because of its solubility properties (e.g., soluble in both alcohol and water) and its resistance to grinding to particle sizes of less than 500 μm. High-molecular weight PEGs are less viscous at melt temperatures than long chain PEO molecules and are soluble in both water and alcohol.

Dyes can also be used and chosen to be soluble in both water and alcohol to produce a dark colored solution upon extraction and filtering as a visual deterrent to abuse. The formulation can include the following components listed in the Table 8 below, including a number of different dyes. Table 8 below lists the components along with their solubility information taken from the various literature sources and tested experimentally (e.g., 200 proof ethanol and filtered through a 0.45 micrometer PTFE filter). The extraction of the active to a pure form can be very difficult using water or alcohol.

TABLE 8

Solubility of the Components of the Present Disclosure Formulation

| Components | Water Solubility | Alcohol Solubility (Literature) | Alcohol Solubility (Tested) |
|---|---|---|---|
| Oxycodone HCl | Yes | Yes | Yes |
| Hydrocodone Bitartrate | Yes | Slightly | N/A |
| Polyethylene Glycol USP NF | Yes | Yes | N/A |
| Anhydrous Citric Acid | Yes | Yes | N/A |
| FD&C Blue #1 | Yes | Yes | Yes |
| FD&C Yellow #6 | Yes | Yes | Yes |
| FD&C Red #40 | Yes | Yes | Yes |

A conventional tablet or powder-filled capsule can be easily crushed to create a fine powder. The waxy material contained in the formulations of the present disclosure can make it difficult to manipulate into particles small enough to be easily absorbed by the nasal mucosa. The waxy material may also congeal once introduced to the semi-aqueous environment of the nasal passages, which can make it difficult to introduce the oxycodone HCl or hydrocodone bitartrate to the bloodstream via the nasal passages.

The formulations of the present disclosure can contain one or more of the following barriers to abuse. Insufflation—The formulation can be formulated to resist grinding to particle sizes of less than about 500 m. Extraction and Purification—The formulation can be formulated with water-and alcohol-soluble dyes to create a dark colored solution upon extraction that can be visually unappealing to intravenous drug users. The water-and alcohol-soluble excipients can present obstacles to purification of the active. In some formulations, if the solvent is flashed off or otherwise evaporated, the excipients can return to the same waxy, dark-colored form as before being introduced to the solvent. Vaporization—The formulation can contain an active, such as oxycodone HCl, which can degrade at temperatures close to where vaporization occurs. Chewing—Because the formulation is an immediate release formulation, it is not expected that crushing or cutting the dosage form will result in an especially rapid release of the drug to produce a "euphoric high."

Table 9 below lists exemplary formulations for the oxycodone HCl abuse deterrent formulation capsules.

TABLE 9

Quantitative Composition of Oxycodone HCl ADF Capsules

| Ingredients | Capsule Quantity (mg) |
| --- | --- |
| Oxycodone HCl USP API | 5-30 |
| Polyethylene Glycol 3350 | 100-150 |
| Polyethylene Glycol 35,000 | 5-25 |
| Anhydrous Citric Acid | 1-2 |
| Dye Blend | |
| FD&C Red #40 (DB-175000) | 0.5-1.0 |
| FD&C Yellow #6 (DB-175000) | 0.3-0.6 |
| FD&C Blue #1 (DB-175000) | 0.1-0.3 |
| Polyethylene Glycol 3350 (DB-175000) | 10-15 |
| Gelatin (Capsule) | |
| Total Fill Weight per Capsule | 100-200 |

Formulations of the present disclosure were manufactured by the following exemplary process. The components of the hot-melt suspension, consisting of Polyethylene Glycol 3350, Polyethylene Glycol 35000, Dye Blend, Grey Powder, Citric Acid and Oxycodone HCl were dispensed according to theoretical batch quantities based on formulation weight percents.

Polyethylene Glycol 3350, Polyethylene Glycol 35000, Dye Blend, Grey Powder, Oxycodone HCl and Citric Acid were added to an Olsa 150 Liter Kettle and heated to a temperature of 70±20° C. Utilizing the homogenizer mixer, external anchor blades and internal mixing blades, the melt was then mixed until uniform Prior to transferring the hot-melt suspension from the kettle to the Shionogi F40 capsule filling machine hopper, a transfer pump and three heat traced hoses were set up and the melt/suspension was recirculated. Mixing and recirculating continued until capsule filling was completed.

The Shionogi F40 capsule filling machine target fill weight was set with an Action Limit of ±3.5% and a Control Limit of ±5.0% plus the average empty capsule weight.

Figure 3:
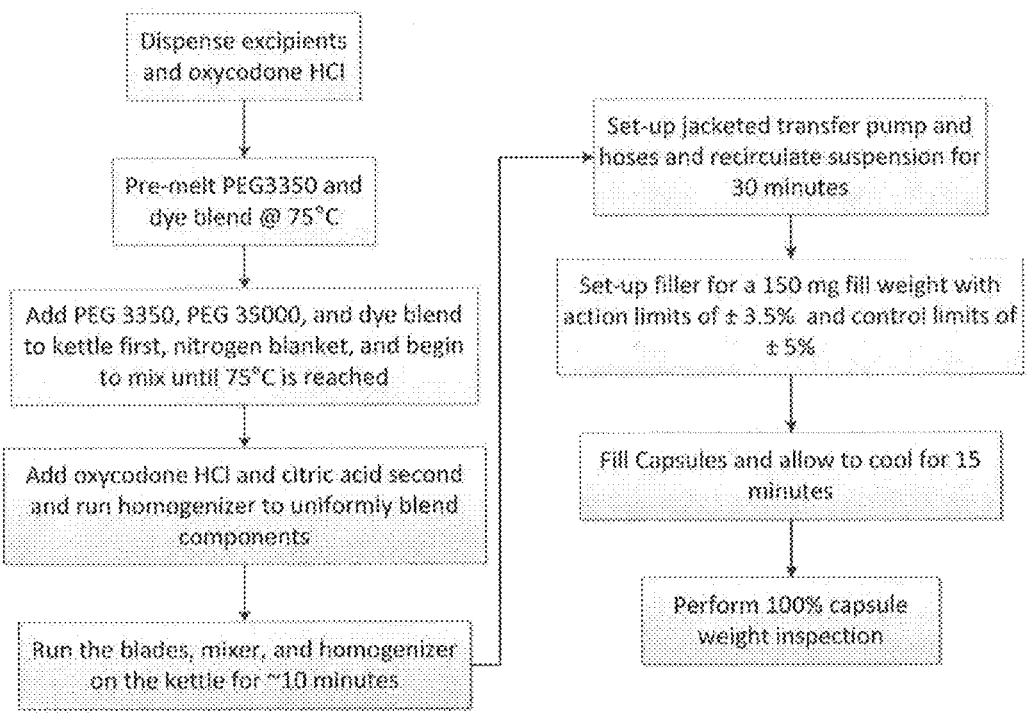
FIG. 3 shows a summary of an exemplary manufacturing process for formulations of the present disclosure.

In-process capsule samples were taken at the beginning, end, and every 30 minutes (for the average capsule weight of 15 filled capsules). Filled capsules were placed onto stainless steel cooling trays and allowed to cure. Following curing, 100% capsule weight inspection was performed using a Shionogi capsule weight inspection machine An exemplary manufacturing process is shown in FIG. 3.

The formulations of the present disclosure are stable upon storage at 25, 30, 35, 40 or 45° C., and at 60%, 65%, 70% or 75% relative humidity, e.g., 30° C./65% RH or 40° C./75% RH. The formulation of the present disclosure can be stable under any of these conditions for up to 1, 2, 3, 4, 5, 6, 9, 12, 16, 18, 24, or 36 months.

Example 5

Abuse Deterrent Properties of Immediate Release Liquid Fill Capsule PEG Formulations In one embodiment, there are at least three determining factors which deem an immediate release drug product "abuse deterrent," namely resistance to grinding, purity upon extraction, and visual evaluation following extraction. Cutting the dosage form can be performed in order to increase the surface area of the product prior to ingesting it in an effort to increase the rate of dissolution into the digestive tract. Cutting can also be used to increase the efficiency of grinding or extraction. Cutting alone, however, is not sufficient to render a formulation abusable. Grinding the dosage form can be performed in order to decrease the particle size of the product more efficiently than cutting in an effort to insufflate (snort) for immediate release into the blood vessels of the nasal passages. A readily available tool used for grinding is a commercially available coffee grinder. In one embodiment, a drug product is considered abuse deterrent if the % material in the pan (≤500 μm) is ≤50%. A dosage form which, when ground, produces ≤50% of the material on a per-dosage form basis available for nasal insufflation (≤500 μm) is considered abuse deterrent. The purpose of this study was to determine the grinding potential of different dosage forms of oxycodone HCl. Texture analysis is the mechanical testing of pharmaceutical products in order to measure their physical properties. The Retsch Knife Mill GRINDOMIX GM200 (TE96) was utilized to mimic a commercially available coffee grinder (Mr. Coffee) in order to grind the drug products into a particle size that is suitable for intranasal abuse (insufflation). Particle size analysis was conducted utilizing an ATM L3P Sonic Sifter (TE147), utilizing a 500 micrometer (μm) particle size sieve (35 mesh). For the purposes of this study, any particle less than 500 μm in diameter is considered suitable for intranasal abuse. It is generally accepted that any particle greater than 500 μm in diameter cannot be sufficiently absorbed by the blood vessels in the nasal passages.

The Retsch Knife Mill GRINDOMIX GM200 utilizes a circular blade attachment to mimic commercially available coffee grinders. The GM200 has a top speed of 10,000 revolutions per minute (rpm), while commercially available coffee grinders have a top speed of approximately 20,000 rpm (an approximate two-fold increase in speed when comparing the GM200 to a Mr. Coffee grinder). However, the approximate two-fold increase in blade diameter (118 mm vs. 60 mm, when comparing the GM200 to a Mr. Coffee grinder, respectively) compensates for the approximate two-fold decrease in top speed via the inversely proportional relationship of the two variables. Further, the torque provided by the GM200 is significantly higher than the torque provided by a Mr. Coffee grinder (0.860 Nm (Newton meters) of the GM200 vs. 0.062 Nm of the Mr. Coffee grinder, respectively), which additionally illustrates the ability (or lack thereof) of the Mr. Coffee grinder to modify the drug products into a particle size suitable for intranasal abuse. The study evaluated the difference in particle sizes of several different formulations of oxycodone HCl following modification (grinding) by the GM200.

Experimental: The samples tested are formulated according to Table 9. The following test equipment was used: Retsch Knife Mill GRINDOMIX GM200 (TE96), ATM L3P Sonic Sifter (TE47), and a 500 µm sieve (35 mesh). The following testing conditions were used: Analysis speed: 10,000 rpm; Analysis time: 30 seconds; Sieve Size: 500 µm (35 mesh); Analysis time: 1 minutes (no pulse). Each sample was prepared in triplicate (N=3).

The composite sample was transferred to a tared weigh boat and the weight of the sample was recorded. The following equation was used to calculate the % sample loss:

$$\text{Sample Loss (\%)} = 100 - \left(\frac{\text{Analyzed Sample (mg)}}{\text{Sample Weight (mg)}} \times 100\right)$$

The weight of the 35 mesh sieve and sample pan was recorded. The testing apparatus was assembled with the 35 mesh sieve above the sample pan. The composite sample was transferred to the testing apparatus and analyzed utilizing the following parameters: 1 minute analysis time and no pulse. The analyzed 35 mesh sieve and sample pan were weighed. The % material remaining on the 35 mesh sieve (≥500 µm) and in the sample pan (≤500 µm) was calculated using the following equation:

$$\text{Percent on Sieve (\%)} = \frac{\text{Weight of Sample on Sieve (mg)}}{\text{Total Weight of Sample on Sieve (mg)}} \times 100$$

Table 10 below shows the particle size after grinding for the oxycodone HCl formulations tested. During testing it was observed by visual observation that the capsule portion of the dosage form of all evaluated batches was not being significantly modified by TE96, and that the majority of the capsule portion remained in the 35 mesh sieve (≥500 µm). The grinding/particle size analysis for this protocol is based on weight differences, which, when the capsule portion is taken into account, can skew the results towards a higher proportion of particles ≥500 µm.

In order to confirm the particle size of capsules modified by TE96, three empty size 3 capsules (N=1) were ground and analyzed. Table 11 shows that for size 3 capsules, 99% of the particles by weight were ≥500 µm. Additional calculations were made which compensated for the percentage of capsules ≥ or <500 µm. These calculations removed the average capsule weight from the analyzed sample by subtracting it from the weight ≥500 µm and the weight <500 µm. The results adjusted for capsule weight are shown in Table 12.

TABLE 10

Particle size after grinding of oxycodone HCl capsules before adjusting for capsule weight. % RSD is percent relative standard deviation

| Location | Replicate | Present Disclosure 5 mg | Present Disclosure 15 mg | Present Disclosure 30 mg |
|---|---|---|---|---|
| 35 Mesh | 1 | 73.2 | 73.8 | 79.0 |
| (≥500 | 2 | 75.9 | 82.2 | 79.2 |
| µm) % | 3 | 72.7 | 78.5 | 77.7 |
|  | Minimum | 72.7 | 73.8 | 77.7 |
|  | Maximum | 75.9 | 82.2 | 79.2 |
|  | Average | 74.0 | 78.1 | 78.7 |
|  | % RSD | 2.3 | 5.4 | 1.0 |
| Pan | 1 | 26.8 | 26.2 | 21.0 |
| (<500 | 2 | 24.1 | 17.8 | 20.8 |
| µm) % | 3 | 27.3 | 21.5 | 22.3 |
|  | Minimum | 24.1 | 17.8 | 20.8 |
|  | Maximum | 27.3 | 26.2 | 22.3 |
|  | Average | 26.0 | 21.9 | 21.3 |
|  | % RSD | 6.6 | 19.3 | 3.8 |

TABLE 11

Particle size of empty size 3 capsules after grinding

| Product | Initial Wt (mg) | After Grinding (mg) | % Loss In Grinding | Tare 35 Mesh (g) | Tare Pan (g) | After 35 Mesh (g) | After Pan (g) | 35 Mesh (≥500 µm) % | Pan (<500 µm) % |
|---|---|---|---|---|---|---|---|---|---|
| Size 3 Capsules | 143.8 | 144.5 | −0.5 | 40.8367 | 4.4111 | 40.9724 | 4.4124 | 99.1 | 0.9 |

As shown in Table 12, after adjusting for the capsule portion, the average percentage of particles ≥500 µm after grinding for the oxycodone HCl capsules ranged from 62.3% to 68.2%. For comparison, approximately 20% of particles by weight of an Immediate Release (IR) Roxicodone® formulation were ≥500 µm after the same grinding procedure.

TABLE 12

Particle size after grinding of oxycodone HCl dosage forms, adjusted for capsule weight. % RSD is percent relative standard deviation.

| Location | Replicate | Present Disclosure 5 mg | Present Disclosure 15 mg | Present Disclosure 30 mg |
|---|---|---|---|---|
| 35 Mesh | 1 | 60.9 | 60.8 | 67.4 |
| (≥500 | 2 | 63.6 | 72.8 | 69.0 |
| µm) % | 3 | 56.3 | 68.0 | 66.9 |
|  | Minimum | 56.3 | 60.8 | 66.9 |
|  | Maximum | 63.6 | 72.8 | 69.0 |

TABLE 12-continued

Particle size after grinding of oxycodone HCl
dosage forms, adjusted for capsule weight.
% RSD is percent relative standard deviation.

| Location | Replicate | Present Disclosure 5 mg | Present Disclosure 15 mg | Present Disclosure 30 mg |
|---|---|---|---|---|
| | Average | 62.3 | 66.8 | 68.2 |
| | % RSD | 6.1 | 9.0 | 1.7 |
| Pan (<500 μm) % | 1 | 39.1 | 39.2 | 32.6 |
| | 2 | 36.4 | 27.2 | 31.0 |
| | 3 | 43.7 | 32.0 | 33.1 |
| | Minimum | 36.4 | 27.2 | 31.0 |
| | Maximum | 43.7 | 39.2 | 33.1 |
| | Average | 39.7 | 32.8 | 32.2 |
| | % RSD | 9.3 | 18.4 | 3.5 |

Table 13 summarizes the grinding results and statistical analysis of the % material ≤500 μm for the Present Disclosure 15 mg and Roxicodone® 15 mg tablets (Mallinckrodt Pharmaceuticals, Inc.).

TABLE 13

Particle Size Analysis of 15 mg Dosages of Roxicodone®
and the Present Disclosure
Grinding Result

| Product | % Particles ≤500 μm | Average | % RSD | F-test | t-test | Statistically Different? |
|---|---|---|---|---|---|---|
| Roxicodone® 15 mg-1 | 76 | 76 | 1.9 | 0.672 | 4.85E−06 | Yes |
| Roxicodone® 15 mg-2 | 75 | | | | | |
| Roxicodone® 15 mg-3 | 78 | | | | | |
| Present Disclosure 15 mg-1 | 43 | 43 | 2.4 | | | |
| Present Disclosure 15 mg-2 | 42 | | | | | |
| Present Disclosure 15 mg-3 | 44 | | | | | |

Another method of rending a drug product abusable is via extraction of the active substance from the dosage form to produce a pure residue. This method can be performed, and is often performed, using a high proof alcohol or an aqueous media. The formulation of the present disclosure can be readily soluble in both aqueous and alcohol environments when the contents are removed from the capsule. Therefore, aqueous and alcohol extraction techniques were evaluated. Solutions were analyzed qualitatively for solution color following filtration, as well as quantitatively for % label claim (LC) (with regards to oxycodone HCl) of solution following filtration. Additionally, evaporated residual samples were analyzed qualitatively for residue color following evaporation, as well as quantitatively for purity determination following the % LC calculations. The quantitative results of the analysis determine the % purity (with regards to oxycodone HC) of the extracted sample solution described above. A drug product can be considered abuse deterrent if the % residue purity is ≤50%. In other embodiments, less than or equal to 40%, 45%, 55%, 60%, 65%, 70% or 75%. Residue purity levels (with regards to the API)≤50% can infer that the excipient load is greater than the API level contained in the residue. In one embodiment, this can be considered abuse deterrent with regards to potential intravenous abuse of a purified residue. Using the data analysis software functionality of Microsoft Excel and a 95% significance interval (p-value=0.05), the F-test and t-tests was analyzed in order to determine if the drug products provide statistically different % purity values.

Tables 14 and 15 show the formulation of the present disclosure results in 9% and 9% purity with regards to oxycodone HCl, in alcohol and aqueous environments, respectively. This is in comparison to Roxicodone® 15 mg, which has a purity of 68% and 19% purity in alcohol and aqueous environments, respectively. This data proves the formulation of the present disclosure is statistically different than Roxicodone® in both alcohol and aqueous extracts.

TABLE 14

% Purity Results—Alcohol

| Product | % Purity | Average | % RSD | F-test | t-test | Statistically Different? |
|---|---|---|---|---|---|---|
| Roxicodone® 15 mg-1 | 66 | 68 | 2.5 | 0.208 | 5.77E−07 | Yes |
| Roxicodone® 15 mg-2 | 69 | | | | | |
| Roxicodone® 15 mg-3 | 68 | | | | | |
| Present Disclosure 15 mg-1 | 10 | 9 | 6.4 | | | |
| Present Disclosure 15 mg-2 | 8 | | | | | |
| Present Disclosure 15 mg-3 | 9 | | | | | |

TABLE 15

% Purity Results—Aqueous

| Product | % Purity | Average | % RSD | F-test | t-test | Statistically Different? |
|---|---|---|---|---|---|---|
| Roxicodone® 15 mg-1 | 20 | 19 | 2.6 | 0.823 | 1.02E−05 | Yes |
| Roxicodone® 15 mg-2 | 19 | | | | | |
| Roxicodone® 15 mg-3 | 19 | | | | | |
| Present Disclosure 15 mg-1 | 10 | 9 | 4.6 | | | |
| Present Disclosure 15 mg-2 | 9 | | | | | |
| Present Disclosure 15 mg-3 | 9 | | | | | |

Color is one identifying characteristic of commercial drug products. Color can be applied to the dosage form in two ways: dye or coating. High potency alcohol (i.e., ≥190 proof (95%)) is one extraction solvent that can be used by abusers for APIs which are insoluble in water or in order to separate the API from other water soluble excipients. Dyes or coatings can potentially be used to alter the physical appearance of the extracted solution of drug product (i.e., turn the resulting solution a noticeable color).

Accordingly, the inclusion of one or more dyes in a drug formulation is one method to render a formulation abuse deterrent. Significant discoloration of an extraction product from a formulation subject to abuse can discourage a potential abuser from using (e.g., injecting or ingesting) the extraction product.

A study was conducted to investigate the effect of dyes in the formulations of the present disclosure. Extraction products from whole formulations were visually inspected to determine abuse deterrence following alcohol extraction. Capsules were added to a flask containing 190 proof ethanol and shaken at 250 rpm for 3 hours. After 3 hours all capsule contents were fully dissolved. Solutions were filtered with a syringe filter and then visually analyzed for color intensity. The samples tested were the immediate release oxycodone HCl capsules according to Table 9 above.

Figure 4:
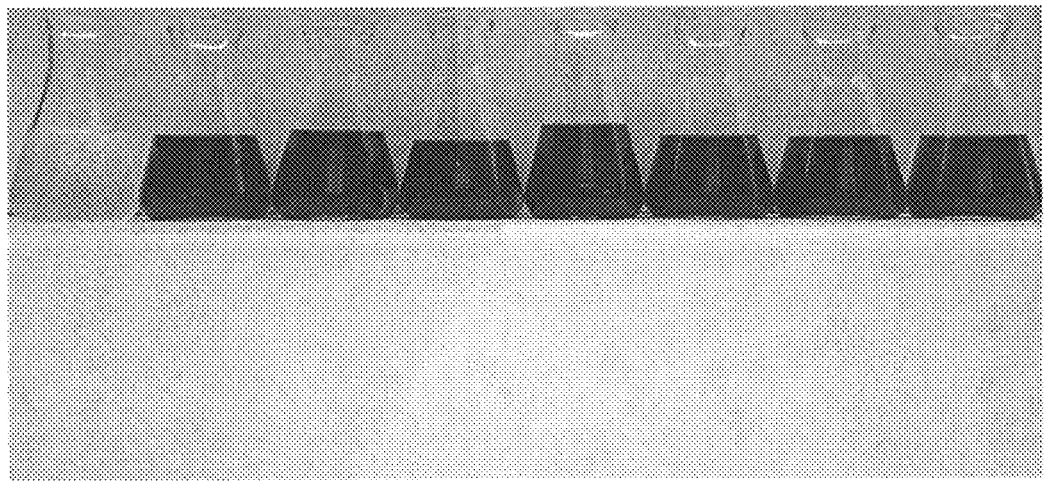
FIG. 4 shows unfiltered solutions of the dosage forms in 190 proof ethanol after shaking at 250 rpm for 3 hours.
Figure 5:
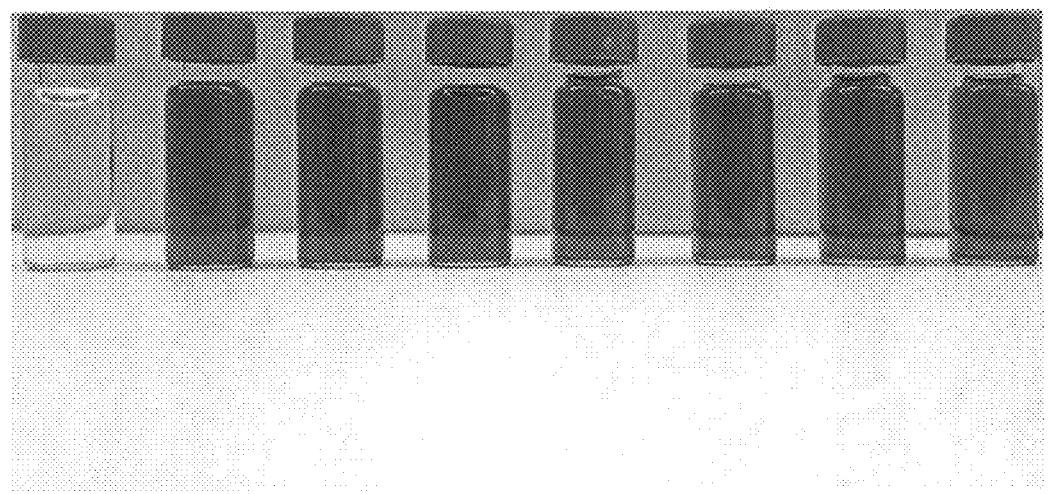
FIG. 5 shows syringe-filtered solutions of the dosage forms in 190 proof ethanol after shaking at 250 rpm for 3 hours.

The unfiltered and filtered solutions are shown in FIGS. 4 and 5, respectively. As shown in Table 16 below, all of the filtered solutions had a color value of 5, indicating that all seven evaluated batches produced a filtered solution which was significantly dark in color. This significant dark color provides potential abuse deterrence to CII narcotic drug products.

TABLE 16

Color Scale Designation—Post-Syringe Filter Analysis for Oxycodone HCl Formulations of the Present Disclosure

| Active thgredient(s) | Color Value |
|---|---|
| 5 mg oxycodone HCl | 5 |
| 15 mg oxycodone HCl | 5 |
| 30 mg oxycodone HCl | 5 |

Additionally, the color of filtered solutions and resulting evaporated residues of alcoholic and aqueous extracts of the formulations of the present disclosure and Roxicodone® were compared. Table 17 below shows both of these dosage forms, with the formulation of the present disclosure providing the most visual deterrence for both the filtered solution and evaporated residue in both media.

TABLE 17

| | | Color Determination | |
|---|---|---|---|
| Product | Solution | Filtered Solution | Evaporated Residue |
| Roxicodone ® 15 mg | Alcohol | 1 | 3 |
| | Aq. | 0 | 3 |
| Present Disclosure 15 mg | Alcohol | 5 | 5 |
| | Aq. | 5 | 5 |

While this disclosure has been particularly shown and described with reference to example embodiments thereof, it will be understood by those skilled in the art that various changes in form and details may be made therein without departing from the scope of the invention encompassed by the appended claims.

We claim:

1. An immediate release, abuse deterrent capsule comprising:
   (a) an active substance susceptible to abuse;
   (b) a first polyethylene glycol (PEG) having an average molecular weight of 35,000 Daltons; and
   (c) a second PEG having an average molecular weight between about 3350 Daltons, wherein the ratio of the first PEG to the second PEG is less than about 1:4 w/w.

2. The capsule of claim 1, wherein the first PEG and the second PEG together are at least about 60 wt % of the dosage form.

3. The capsule of claim 1, wherein at least 80% of the contents are soluble both water and alcohol.

4. The capsule of claim 1, wherein the active substance is hydrocodone bitartrate.

5. The capsule of claim 1, wherein the active substance is oxycodone HCl.

6. The capsule of claim 1, further comprising a grey dye comprising FD&C Blue #1, FD&C Yellow #6, and FD&C Red #40.

7. The capsule of claim 6, wherein the dye provides a visual deterrent to abuse.

8. The capsule of claim 1, wherein the ratio of the first PEG to the second PEG is between about 1:7 w/w and about 1:11 w/w.

9. The capsule of claim 1, wherein the capsule comprises at least about 2.5 wt % of the active substance.

10. The capsule of claim 1, wherein the capsule is prepared by filling a capsule body with a heated homogenized suspension comprising the active substance, the first PEG and the second PEG.

11. A process for the production of an immediate release, abuse deterrent capsule comprising at least one active substance susceptible to abuse comprising:
   (a) preparing a homogenized suspension of:
      (i) the at least one active substance susceptible to abuse;
      (ii) a first PEG having an average molecular weight of 35,000 Daltons; and
      (iii) a second PEG having an average molecular weight of 3350 Daltons; and
   (b) filling the homogenized suspension into a capsule body to produce the capsule, wherein the ratio of the first PEG to the second PEG is less than about 1:4 w/w.

12. The process of claim 11, wherein the first PEG and the second PEG together are at least about 60 wt % of the capsule.

13. The process of claim 11, wherein the active substance is hydrocodone bitartrate.

14. The process of claim 11, wherein the active substance is oxycodone HCl.

15. The process of claim 11, wherein the capsule is formed by joining a capsule body with a capsule cap.

16. A method of treating pain comprising administering to a subject in need thereof a therapeutically effective amount of the capsule of claim 1.

* * * * *